(12) United States Patent
Beckert et al.

(10) Patent No.: US 8,993,248 B2
(45) Date of Patent: Mar. 31, 2015

(54) TRUNCATED HUMAN VITAMIN D BINDING PROTEIN AND MUTATION AND FUSION THEREOF AND RELATED MATERIALS AND METHODS OF USE

(71) Applicant: Abbott Laboratories, Abbott Park, IL (US)

(72) Inventors: Christian Beckert, Wiesbaden (DE); Susan E. Brophy, Lindenhurst, IL (US); Jonathan Grote, Green Oaks, IL (US); Dagang Huang, Shanghai (CN); Jan Schultess, Mainz (DE); Bailin Tu, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/726,219

(22) Filed: Dec. 23, 2012

(65) Prior Publication Data
US 2013/0295593 A1 Nov. 7, 2013

Related U.S. Application Data

(60) Provisional application No. 61/582,292, filed on Dec. 31, 2011, provisional application No. 61/660,786, filed on Jun. 17, 2012.

(51) Int. Cl.
| | | |
|---|---|---|
| *C07K 14/00* | (2006.01) | |
| *C07K 14/435* | (2006.01) | |
| *G01N 33/53* | (2006.01) | |
| *G01N 33/82* | (2006.01) | |
| *C07K 14/76* | (2006.01) | |
| *C07K 14/47* | (2006.01) | |
| *G01N 33/543* | (2006.01) | |

(52) U.S. Cl.
CPC ............... *G01N 33/82* (2013.01); *C07K 14/76* (2013.01); *C07K 14/47* (2013.01); *C07K 2319/00* (2013.01); *C07K 2319/30* (2013.01); *C07K 2319/40* (2013.01); *G01N 33/543* (2013.01)
USPC ........................................ 435/7.1; 530/350

(58) Field of Classification Search
CPC ................................ G01N 33/82; C07K 14/47
USPC ........... 435/7.93, 328, 358, 320.1; 530/387.3, 530/395; 536/23.5
See application file for complete search history.

(56) References Cited

U.S. PATENT DOCUMENTS

| 7,087,395 B1 | 8/2006 | Garrity et al. |
| 7,482,162 B2 | 1/2009 | Laurie et al. |
| 2004/0132104 A1 | 7/2004 | Sackrison et al. |
| 2006/0094659 A1 | 5/2006 | Kew et al. |

FOREIGN PATENT DOCUMENTS

| EP | 2372365 | 10/2011 |
| WO | WO 02/057797 | 7/2002 |
| WO | WO 2006/041829 | 4/2006 |
| WO | WO 2013/102149 | 7/2012 |

OTHER PUBLICATIONS

Calvo, "Relations Between Vitamin D And Fatty Acid Binding Properties Of Vitamin D-Binding Protein," *Biochem. Biophys. Res. Comm.* 163: 14-17 (1989).
Cleve et al., "The Mutants of the Vitamin-D-Binding Protein: More than 120 Variants of the GC/DBP System," *Vox Sang.* 54: 215-225 (1988).
Friguet et al., "Measurements of the True Affinity Constant in Solution of Antigen-Antibody Complexes by Enzyme-Linked Immunosorbent Assay," *J. Immunolog. Methods* 77: 305-319 (1985).
Haddad et al., "Identification of the Sterol—and Actin-Binding Domains of Plasma Vitamin D Binding Protein (Gc-Globulin)," *Biochem.* 31: 7174-7181 (1992).
Head et al., "Crystal Structure of the Complex between Actin and Human Vitamin D-Binding Protein at 2.5 Å Resolution," *Biochem.* 41: 9015-9020 (2002).
Hollis, "Assessment of Circulating 25(OH)D and 1,25(OH)2D: Emergence as Clinically Important Diagnostic Tools," *Nutrition Reviews* 65(8): S87-S90 (2007).
Malloy et al., "A Novel Mutation in Helix 12 of the Vitamin D Receptor Impairs coactivator Interaction and Causes Hereditary 1,25-Dihydroxyvitamin D-Resistant Rickets without Alopecia," *Mol. Endocr.* 16(11): 2538-2546 (2002).
Malloy et al., "A Unique Insertion/Substitution in Helix H1 of the Vitamin D Receptor Ligand Binding Domain in a Patient With Hereditary 1,25-Dihydroxyvitamin D-Resistant Rickets," *J. Bone & Min. Res.* 19(6): 1018-1024 (2004).
Otterbein et al., "Crystal structures of the vitamin D-binding protein and its complex with actin: Structural basis of the actin-scavenger system," *PNAS USA* 99(12): 8003-8008 (2002).
Souberbielle et al., "Vitamin D and musculoskeletal health, cardiovascular disease, autoimmunity and cancer: Recommendations for clinical practice," *Autoimmun. Rev.* 9: 709-715 (2010).
Speeckaert et al., "Biological and clinical aspects of the vitamin D binding protein (GC-globulin) and its polymorphism," *Clinica Chimica Acta* 372: 33-42 (2006).
Swamy et al., "Biochemical and preliminary crystallographic characterization of the vitamin D sterol—and actin-binding by human vitamin D-binding protein," *Arch. Biochem. Biophys.* 402: 14-23 (2002).
Swamy et al., "Roles of the Structure and Orientation of Ligands and Ligand Mimics inside the Ligand-Binding Pocket of the Vitamin D-Binding Protein," *Biochem.* 36: 7432-7436 (1997).

(Continued)

*Primary Examiner* — David J Steadman
*Assistant Examiner* — Paul Holland
(74) *Attorney, Agent, or Firm* — Audrey L. Bartnicki; Carol Larcher; Larcher & Chao Law Group

(57) ABSTRACT

Vitamin D binding proteins (DBP), in particular truncated DBP and mutated, truncated DBP, as well as fusion proteins thereof, nucleic acid molecules encoding same, vectors, host cells, and methods, kits and solid supports for determining the total amount of 25-hydroxy vitamin $D_2$ and 25-hydroxy vitamin $D_3$ in a test sample.

23 Claims, 7 Drawing Sheets

(56) References Cited

OTHER PUBLICATIONS

Veroven et al., "A structural basis for the unique binding features of the human vitamin D-binding protein," *Nat. Sruct. Bio*, 9(2): 131-136 (2002).

White et al., "The Multifunctional Properties and Characteristics of Vitamin D-Binding Protein," *Trends Endocrinol. Metab*. 11(8): 320-327 (2000).

Zhang et al., "Identification of two distinct cell binding sequences in the vitamin D binding protein," *Biochimica et Biophysica* 1803: 623-629 (2010).

International Search Report and Written Opinion for Application No. PCT/US2012/072189, mailed on Jun. 4, 2013, 14 pages.

Cooke et al., "Vitamin D Binding Protein," *In: Vitamin D*, Feldman et al., eds., Academic Press, pp. 87-101 (1997).

PCT International Preliminary Report on Patentability and Written Opinion dated Jul. 1, 2014 issued in PCT/US2012/072189; 7 Pages.

TTAGAGAGAGGCCGGGATTATGAAAAGAATAAAGTCTGCAAGGAATTCTCCCAT
CTGGGAAAGGAGGACTTCACATCTCTGTCACTAGTCCTGTACAGTAGAAAATTTC
CCAGTGGCACGTTTGAACAGGTCAGCCAACTTGTGAAGGAAGTTGTCTCCTTGAC
CGAAGCCTGCTGTGCGGAAGGGGCTGACCCTGACTGCTATGACACCAGGACCTC
AGCACTG*GCT*GCCAAG*GCC*TGTGAAAGTAATTCTCCATTCCCCGTTCACCCAGGC
ACTGCTGAGTGCTGCACCAAAGAGGGCCTGGAACGAAAGCTCTGCATGGCTGCT
CTGAAACACCAGCCACAGGAATTCCCCACCTACGTGGAACCCACAAATGATGAA
ATCTGTGAGGCGTTCAGGAAAGATCCAAAGGAATATGCTAATCAATTTATGTGG
GAATATTCCACTAATTACGGCCAAGCTCCTCTGTCACTTTTAGTCAGTTACACCA
AGAGTTATCTTTCTATGGTAGGGTCCTGCTGTACCTCTGCAAGCCCAACTGTATG
CTTTTTGAAAGAGAGACTCCAGCTTAAACATTTATCACTTCTCACCACTCTGTCAA
ATAGAGTCTGCTCACAATATGCTGCTTATGGG [SEQ ID NO:1]

Fig. 1

LERGRDYEKNKVCKEFSHLGKEDFTSLSLVLYSRKFPSGTFEQVSQLVKEVVSLTEA
CCAEGADPDCYDTRTSA*LA*AK*A*CESNSPFPVHPGTAECCTKEGLERKLCMAALKHQ
PQEFPTYVEPTNDEICEAFRKDPKEYANQFMWEYSTNYGQAPLSLLVSYTKSYLSMV
GSCCTSASPTVCFLKERLQLKHLSLLTTLSNRVCSQYAAYG [SEQ ID NO:2]

Fig. 2

GAGAAGAAATCAAGGCTCAGCAATCTCATAAAGTTAGCCCAAAAAGTGCCTACT
GCTGATCTGGAGGATGTTTTGCCACTAGCTGAAGATATTACTAACATCCTCTCCA
AATGCTGTGAGTCTGCCTCTGAAGATTGCATGGCCAAAGAGCTGCCTGAACACAC
AGTA [SEQ ID NO:3]

Fig. 3

EKKSRLSNLIKLAQKVPTADLEDVLPLAEDITNILSKCCESASEDCMAKELPEHTV
[SEQ ID NO:4]

Fig. 4

TTAGAGAGAGGCCGGGATTATGAAAAGAATAAAGTCTGCAAGGAATTCTCCCAT
CTGGGAAAGGAGGACTTCACATCTCTGTCACTAGTCCTGTACAGTAGAAAATTTC
CCAGTGGCACGTTTGAACAGGTCAGCCAACTTGTGAAGGAAGTTGTCTCCTTGAC
CGAAGCCTGCTGTGCGGAAGGGGCTGACCCTGACTGCTATGACACCAGGACCTC
AGCACTG*GCT*GCCAAG*GCC*TGTGAAAGTAATTCTCCATTCCCCGTTCACCCAGGC
ACTGCTGAGTGCTGCACCAAAGAGGGCCTGGAACGAAAGCTCTGCATGGCTGCT
CTGAAACACCAGCCACAGGAATTCCCCACCTACGTGGAACCCACAAATGATGAA
ATCTGTGAGGCGTTCAGGAAAGATCCAAAGGAATATGCTAATCAATTTATGTGG
GAATATTCCACTAATTACGGCCAAGCTCCTCTGTCACTTTTAGTCAGTTACACCA
AGAGTTATCTTTCTATGGTAGGGTCCTGCTGTACCTCTGCAAGCCCAACTGTATG
CTTTTTGAAAGAGAGACTCCAGCTTAAACATTTATCACTTCTCACCACTCTGTCAA
ATAGAGTCTGCTCACAATATGCTGCTTATGGGGAGAAGAAATCAAGGCTCAGCA
ATCTCATAAAGTTAGCCCAAAAAGTGCCTACTGCTGATCTGGAGGATGTTTTGCC
ACTAGCTGAAGATATTACTAACATCCTCTCCAAATGCTGTGAGTCTGCCTCTGAA
GATTGCATGGCCAAAGAGCTGCCTGAACACACAGTA [SEQ ID NO:5]

Fig. 5

LERGRDYEKNKVCKEFSHLGKEDFTSLSLVLYSRKFPSGTFEQVSQLVKEVVSLTEA
CCAEGADPDCYDTRTSAL*A*AK*A*CESNSPFPVHPGTAECCTKEGLERKLCMAALKHQ
PQEFPTYVEPTNDEICEAFRKDPKEYANQFMWEYSTNYGQAPLSLLVSYTKSYLSMV
GSCCTSASPTVCFLKERLQLKHLSLLTTLSNRVCSQYAAYGEKKSRLSNLIKLAQKVP
TADLEDVLPLAEDITNILSKCCESASEDCMAKELPEHTV [SEQ ID NO:6]

Fig. 6

AAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTG
AGGTCACATGCGTGGTGGTGGACGTGAGCCACGAAGACCCTGAGGTCAAGTTCA
ACTGGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCAGG
ACTGGCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCACAGG
TGTACACCCTGCCCCCATCCCGCGAGGAGATGACCAAGAACCAGGTCAGCCTGA
CCTGCCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAGG
GGAACGTCTTCTCATGCTCCGTGATGCATGAGGCTCTGCACAACCACTACACGCA
GAAGAGCCTCTCCCTGTCTCCGGGTAAATGA [SEQ ID NO:7]

Fig. 7

KTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK
[SEQ ID NO:8]

Fig. 8

TTAGAGAGAGGCCGGGATTATGAAAAGAATAAAGTCTGCAAGGAATTCTCCCAT
CTGGGAAAGGAGGACTTCACATCTCTGTCACTAGTCCTGTACAGTAGAAAATTTC
CCAGTGGCACGTTTGAACAGGTCAGCCAACTTGTGAAGGAAGTTGTCTCCTTGAC
CGAAGCCTGCTGTGCGGAAGGGGCTGACCCTGACTGCTATGACACCAGGACCTC
AGCACTG*GCT*GCCAAG*GCC*TGTGAAAGTAATTCTCCATTCCCCGTTCACCCAGGC
ACTGCTGAGTGCTGCACCAAAGAGGGCCTGGAACGAAAGCTCTGCATGGCTGCT
CTGAAACACCAGCCACAGGAATTCCCCACCTACGTGGAACCCACAAATGATGAA
ATCTGTGAGGCGTTCAGGAAAGATCCAAAGGAATATGCTAATCAATTTATGTGG
GAATATTCCACTAATTACGGCCAAGCTCCTCTGTCACTTTTAGTCAGTTACACCA
AGAGTTATCTTTCTATGGTAGGGTCCTGCTGTACCTCTGCAAGCCCAACTGTATG
CTTTTTGAAAGAGAGACTCCAGCTTAAACATTTATCACTTCTCACCACTCTGTCAA
ATAGAGTCTGCTCACAATATGCTGCTTATGGGGAGAAGAAATCAAGGCTCAGCA
ATCTCATAAAGTTAGCCCAAAAAGTGCCTACTGCTGATCTGGAGGATGTTTTGCC
ACTAGCTGAAGATATTACTAACATCCTCTCCAAATGCTGTGAGTCTGCCTCTGAA
GATTGCATGGCCAAAGAGCTGCCTAACACACAGTAAAAACTCACACATGCCCA
CCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCAT
CCCGCGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCT
CCGGGTAAATGA [SEQ ID NO:9]

Fig. 9

LERGRDYEKNKVCKEFSHLGKEDFTSLSLVLYSRKFPSGTFEQVSQLVKEVVSLTEA
CCAEGADPDCYDTRTSALAAKACESNSPFPVHPGTAECCTKEGLERKLCMAALKHQ
PQEFPTYVEPTNDEICEAFRKDPKEYANQFMWEYSTNYGQAPLSLLVSYTKSYLSMV
GSCCTSASPTVCFLKERLQLKHLSLLTTLSNRVCSQYAAYGEKKSRLSNLIKLAQKVP
TADLEDVLPLAEDITNILSKCCESASEDCMAKELPEHTVKTHTCPPCPAPELLGGPSVF
LFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLT
VDKSRWQQGNVFSCSVMHEALHNHYTQKSLSLSPGK [SEQ ID NO:10]

Fig. 10

TTAGAGAGAGGCCGGGATTATGAAAAGAATAAAGTCTGCAAGGAATTCTCCCAT
CTGGGAAAGGAGGACTTCACATCTCTGTCACTAGTCCTGTACAGTAGAAAATTTC
CCAGTGGCACGTTTGAACAGGTCAGCCAACTTGTGAAGGAAGTTGTCTCCTTGAC
CGAAGCCTGCTGTGCGGAAGGGGCTGACCCTGACTGCTATGACACCAGGACCTC
AGCACTG*TCT*GCCAAG*TCC*TGTGAAAGTAATTCTCCATTCCCCGTTCACCCAGGC
ACTGCTGAGTGCTGCACCAAAGAGGGCCTGGAACGAAAGCTCTGCATGGCTGCT
CTGAAACACCAGCCACAGGAATTCCCCACCTACGTGGAACCCACAAATGATGAA
ATCTGTGAGGCGTTCAGGAAAGATCCAAAGGAATATGCTAATCAATTTATGTGG
GAATATTCCACTAATTACGGCCAAGCTCCTCTGTCACTTTTAGTCAGTTACACCA
AGAGTTATCTTTCTATGGTAGGGTCCTGCTGTACCTCTGCAAGCCCAACTGTATG
CTTTTTGAAAGAGAGACTCCAGCTTAAACATTTATCACTTCTCACCACTCTGTCAA
ATAGAGTCTGCTCACAATATGCTGCTTATGGG [SEQ ID NO:11]

Fig. 11

LERGRDYEKNKVCKEFSHLGKEDFTSLSLVLYSRKFPSGTFEQVSQLVKEVVSLTEA
CCAEGADPDCYDTRTSAL*S*AK*S*CESNSPFPVHPGTAECCTKEGLERKLCMAALKHQP
QEFPTYVEPTNDEICEAFRKDPKEYANQFMWEYSTNYGQAPLSLLVSYTKSYLSMV
GSCCTSASPTVCFLKERLQLKHLSLLTTLSNRVCSQYAAYG [SEQ ID NO:12]

Fig. 12

TTAGAGAGAGGCCGGGATTATGAAAAGAATAAAGTCTGCAAGGAATTCTCCCAT
CTGGGAAAGGAGGACTTCACATCTCTGTCACTAGTCCTGTACAGTAGAAAATTTC
CCAGTGGCACGTTTGAACAGGTCAGCCAACTTGTGAAGGAAGTTGTCTCCTTGAC
CGAAGCCTGCTGTGCGGAAGGGGCTGACCCTGACTGCTATGACACCAGGACCTC
AGCACTG*TCT*GCCAAG*TCC*TGTGAAAGTAATTCTCCATTCCCCGTTCACCCAGGC
ACTGCTGAGTGCTGCACCAAAGAGGGCCTGGAACGAAAGCTCTGCATGGCTGCT
CTGAAACACCAGCCACAGGAATTCCCCACCTACGTGGAACCCACAAATGATGAA
ATCTGTGAGGCGTTCAGGAAAGATCCAAAGGAATATGCTAATCAATTTATGTGG
GAATATTCCACTAATTACGGCCAAGCTCCTCTGTCACTTTTAGTCAGTTACACCA
AGAGTTATCTTTCTATGGTAGGGTCCTGCTGTACCTCTGCAAGCCCAACTGTATG
CTTTTTGAAAGAGAGACTCCAGCTTAAACATTTATCACTTCTCACCACTCTGTCAA
ATAGAGTCTGCTCACAATATGCTGCTTATGGGGAGAAGAAATCAAGGCTCAGCA
ATCTCATAAAGTTAGCCCAAAAAGTGCCTACTGCTGATCTGGAGGATGTTTTGCC
ACTAGCTGAAGATATTACTAACATCCTCTCCAAATGCTGTGAGTCTGCCTCTGAA
GATTGCATGGCCAAAGAGCTGCCTGAACACACAGTA [SEQ ID NO:13]

Fig. 13

LERGRDYEKNKVCKEFSHLGKEDFTSLSLVLYSRKFPSGTFEQVSQLVKEVVSLTEA
CCAEGADPDCYDTRTSALSAKSCESNSPFPVHPGTAECCTKEGLERKLCMAALKHQP
QEFPTYVEPTNDEICEAFRKDPKEYANQFMWEYSTNYGQAPLSLLVSYTKSYLSMV
GSCCTSASPTVCFLKERLQLKHLSLLTTLSNRVCSQYAAYGEKKSRLSNLIKLAQKVP
TADLEDVLPLAEDITNILSKCCESASEDCMAKELPEHTV [SEQ ID NO:14]

Fig. 14

TRUNCATED HUMAN VITAMIN D BINDING PROTEIN AND MUTATION AND FUSION THEREOF AND RELATED MATERIALS AND METHODS OF USE

CROSS-REFERENCE TO RELATED APPLICATIONS

This application claims the priority of U.S. Provisional Patent Application 61/582292 filed on Dec. 31, 2011 (pending), and of U.S. Provisional Patent Application 61/660786 filed on Jun. 17, 2012 (pending), each incorporated by reference in their entirety.

SEQUENCE LISTING

The instant application contains a Sequence Listing which has been submitted in ASCII format via EFS-Web and is hereby incorporated by reference in its entirety. Said ASCII copy, created on Dec. 27, 2012, is named 10988USO1_SEQ_ST.txt. and is 23,683 bytes in size.

TECHNICAL FIELD

The present disclosure relates to binding proteins, in particular truncated binding proteins and mutated, truncated binding proteins, as well as fusion proteins, nucleic acid molecules, vectors, host cells, and methods, kits and solid supports for determining the total amount of an analyte in a test sample.

BACKGROUND

Vitamin D is a group of prohormones. The two major forms of vitamin D are vitamin $D_2$ and vitamin $D_3$. Vitamin D is metabolized to 25-hydroxy vitamin D (calcidiol) in the kidney and 1,25-dihydroxy vitamin D (calcitriol) in the liver.

Vitamin D facilitates the flow of calcium into the bloodstream. The flow of calcium into the bloodstream is important for the mineralization of bone and the prevention of hypocalcemic tetany.

Vitamin D assays have become increasingly popular in North America. The development of highly specific anti-vitamin D monoclonal antibodies for vitamin D assays, however, has proven challenging. Various animal immunization protocols have been carried out in efforts to produce monoclonal antibodies specific for 25-hydroxy vitamin $D_2$ and 25-hydroxy vitamin $D_3$. The combined measurement of 25-hydroxy vitamin $D_2$ and 25-hydroxy vitamin $D_3$ (collectively, 25-hydroxy vitamin D) is considered to be the best indicator of the total amount of vitamin D in the body.

Vitamin D hormones have essential roles in human health mediated by intracellular vitamin D receptors (VDR). For instance, the vitamin D hormones regulate blood calcium levels by controlling the absorption of dietary calcium by the small intestine and the reabsorption of calcium by the kidneys. Excessive hormone levels can lead to abnormally elevated urine calcium (hypercalciuria), blood calcium (hypercalcemia) and blood phosphorus (hyperphosphatemia). Vitamin D hormones also participate in the regulation of cellular differentiation and growth, parathyroid hormone (PTH) secretion by the parathyroid glands, and normal bone formation and metabolism. Furthermore, vitamin D hormones are required for the normal functioning of the musculoskeletal, immune and rennin/angiotensin systems. Numerous other roles for the vitamin D hormones have been identified and proposed based on the documented presence of intracellular VDR in nearly every human tissue.

Vitamin D binding protein (DBP) is a triple-domain, monomeric glycoprotein that occurs naturally in mammals. It is a member of the albumin, α-fetoprotein, and α-albumin/afamin gene family. Initially, DBP was named group-specific component of serum (Gc-globulin). The majority of serum DBP is expressed and secreted from the liver. It binds, solubilizes, and transports vitamin D in blood with binding affinities ranging from about 2 nM to about 20 nM (White et al., Trends Endocrinol. Metab. 11: 320-327 (2000); and Cooke et al., "Vitamin D binding protein," In: Vitamin D, Feldman et al., eds., Academic Press (1997), pages 87-101). DBP also binds to G-actin (Speeckaert et al., Clinica Chimica Acta 372: 33-42 (2006)), which is released from cells to the blood upon injury, with a binding affinity of about 10 nM, and fatty acids (Calvo, Biochem. Biophys. Res. Comm 163: 14-17 (1989)). Human DBP has dominant alleles, namely GC1F, GC1S and GC2, and over 124 other alleles (Cleve et al., Vox Sang. 54: 215-225 (1988)). The normal adult level of DBP is 4-8 μM (200-400 mg/L), which is about 20-100 fold higher than its ligands, namely vitamin D and its metabolites (White et al. (2000), supra). Structural and biochemical characterization has revealed that domain I of DBP (amino acids 1-191) binds vitamin D (specifically amino acids 35-49 of domain I (confirmed by crystal structure)), whereas domain III (amino acids 379-458) binds G-actin (specifically amino acids 373-403 of domain III (crystal structure indicates actin interacts with distinct amino acid sequences in all of the three domains)) (Haddad et al., Biochemistry 31: 7174-7181 (1992); Swamy et al., Biochem. 36: 7432-7436 (1997); Verboven et al., Nature Structural Biology 9: 131-136 (2002); Swamy et al., Arch. Biochem. Biophys. 402: 14-23 (2002); Head et al., Biochem. 41: 9015-9020 (2002); and Otterbein et al., PNAS USA 99: 8003-8008 (2002)). Human DBP has 458 amino acids (after cleavage of a 16-amino acid signal peptide), a high cysteine content (28 cysteines, all in disulfide form), and a molecular weight of 52 kD and migrates at 58 kD on an SDS-PAGE gel. Analysis of truncated proteins and overlapping peptides has indicated that cell binding is mediated by amino acids 150-172 of domain I and amino acids 379-402 of domain III (Zhang et al. Biochim Biophys. Acta 1803: 623-629 (2010)).

Competitive protein-binding assays for 25-hydroxy vitamin D and 1,25-dihydroxy vitamin D were introduced more than three decades ago, and were based on assessing circulating 25-hydroxy vitamin D or 1,25 dihydroxy-vitamin D using the DBP or chick intestinal receptor, respectively, as the primary binding agents (Hollis, Nutrition Reviews 65(8): S87-S90 (August 2007 (II)). Both assays employed $^3$H-labeled compounds as reporters, and, while valid, they were cumbersome. Since then, assays for both metabolites have advanced and include the use of various methods, such as radioimmunoassay, enzyme-linked immunoassay, high-performance liquid chromatography, liquid chromatography coupled with mass spectrometry, and random access automated assay based on chemiluminescence. U.S. Pat. No. 7,087,395 discloses the use of a releasing composition including cyclodextrin, sodium salicylate, and sodium hydroxide, 25-hydroxy vitamin D coupled to a solid phase, DBP, and labeled anti-DBP antibody, which produces a detectable signal in the presence of 25-hydroxy vitamin D, to determine the amount of 25-hydroxy vitamin D in a sample. U.S. Pat. No. 7,482,162 B discloses adding a non-competitive displacement agent comprising 8-anilino-1-napthalene-sulfonic acid ammonium salt, 3-(acetonylbenzyl)-4-hydroxy-coumarin and a water-miscible solvent, to a serum or plasma sample to separate any vitamin D metabolite in the sample from protein to which the vitamin D metabolite is bound, such that any separated vitamin D metabolite can be captured, contacting the sample with a support having immobilized thereon a binding factor to capture any vitamin D metabolite separated from protein, and measuring the captured vitamin D metabolite.

The present disclosure seeks to provide a quantitative vitamin D assay using a mutated, truncated DBP fused to human IgG constant fragment (Fc) that binds specifically to 25-hydroxy vitamin $D_2$ and 25-hydroxy vitamin $D_3$. This and other objects and advantages, as well as inventive features, will become apparent from the detailed description provided herein.

SUMMARY

A truncated vitamin D binding protein (DBP) consisting essentially of domain I and α-helix 1 of domain II is provided. The truncated DBP can consist essentially of amino acids 1-211. The truncated DBP can consist essentially of SEQ ID NO:12.

A mutated truncated DBP consisting essentially of domain I and α-helix 1 of domain II in which amino acid 76 is mutated, amino acid 79 is mutated, or amino acid 76 and amino acid 79 are mutated is also provided. The mutated truncated DBP can consist essentially of amino acids 1-211 in which amino acid 76 is mutated, amino acid 79 is mutated, or amino acid 76 and amino acid 79 are mutated. The mutated truncated DBP can consist essentially of SEQ ID NO:12 in which serine 76 is mutated, serine 79 is mutated, or serine 76 and serine 79 are mutated. The mutated truncated DBP can consist essentially of SEQ ID NO:2.

Another mutated truncated DBP is also provided. The mutated truncated DBP consists essentially of domain I and α-helix 1, α-helix 2, α-helix 3, and part or all of α-helix 4 in which amino acid 76 is mutated, amino acid 79 is mutated, or amino acid 76 and amino acid 79 are mutated. The mutated truncated DBP can consist essentially of amino acids 1-267 in which amino acid 76 is mutated, amino acid 79 is mutated, or amino acid 76 and amino acid 79 are mutated. The mutated truncated DBP can consist essentially of SEQ ID NO:14 in which serine 76 is mutated, serine 79 is mutated, or serine 76 and serine 79 are mutated. The mutated truncated DBP can consist essentially of SEQ ID NO:6.

A fusion protein is further provided. The fusion protein comprises:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, or (k) a mutated truncated DBP consisting essentially of SEQ ID NO:6.

The fusion protein can further comprise a human IgG1 constant fragment (hFc). For example, the fusion protein can further comprise the amino acid sequence of SEQ ID NO:10.

Also provided is an isolated or purified nucleic acid molecule comprising a nucleotide sequence encoding:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, or (k) a mutated truncated DBP consisting essentially of SEQ ID NO:6, wherein the isolated or purified nucleic acid molecule can be a vector.

The isolated or purified nucleic acid molecule can comprise the nucleotide sequence of SEQ ID NO:11, SEQ ID NO:1, or SEQ ID NO:5.

In view of the above, a host cell is provided. The host cell comprises an above-described isolated or purified nucleic acid molecule comprising a nucleotide sequence encoding a truncated DBP or a mutated truncated DBP.

An isolated or purified nucleic acid molecule comprising a nucleotide sequence encoding an above-described fusion protein is also provided. The isolated or purified nucleic acid molecule can be a vector. The isolated or purified nucleic acid molecule can comprise the nucleotide sequence of SEQ ID NO:9.

In view of the above, another host cell is provided. The host cell comprises and expresses an above-described isolated or purified nucleic acid molecule comprising a nucleotide sequence encoding a fusion protein. The host cell can be a Chinese hamster ovary (CHO) cell, or any other appropriate cell allowing protein production.

Additionally provided is a solid support to which is attached:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated,
(e) a mutated truncated DBP consisting essentially of amino acids 1-211 in which amino acid 76 is mutated, amino acid 79 is mutated, or amino acid 76 and amino acid 79 are mutated,
(f) a mutated truncated DBP consisting essentially of SEQ ID NO:12 in which serine 76 is mutated, serine 79 is mutated, or serine 76 and serine 79 are mutated,
(g) a mutated truncated DBP consisting essentially of SEQ ID NO:2,
(h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6, or
(l) a fusion protein comprising (a), (b), (c), (d), (e), (f), (g), (h), (i), (j), or (k). The fusion protein can comprise a human IgG1 constant fragment (hFc). For example, the fusion protein can comprise the amino acid sequence of SEQ ID NO:10.

A kit for assay of 25-hydroxy vitamin $D_2$ and 25-hydroxy vitamin $D_3$ is also provided. The kit comprises:
(i) instructions for assaying a test sample for 25-hydroxy vitamin $D_2$ and 25-hydroxy vitamin $D_3$ and
(ii) one or more of:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated,
(e) a mutated truncated DBP consisting essentially of amino acids 1-211 in which amino acid 76 is mutated, amino acid 79 is mutated, or amino acid 76 and amino acid 79 are mutated,
(f) a mutated truncated DBP consisting essentially of SEQ ID NO:12 in which serine 76 is mutated, serine 79 is mutated, or serine 76 and serine 79 are mutated,
(g) a mutated truncated DBP consisting essentially of SEQ ID NO:2,
(h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6,
(l) a fusion protein comprising (a), (b), (c), (d), (e), (f), (g), (h), (i), (j), or (k), and
(m) a solid support comprising (a), (b), (c), (d), (e), (f), (g), (h), (i), (j), (k), or (l),
wherein any of (a)-(m) can be detectably labeled.

A method of determining the total amount of 25-hydroxy vitamin $D_2$ and 25-hydroxy vitamin $D_3$ in a test sample is also provided. The method comprises:
(i) contacting the test sample with a DBP, wherein the DBP is selected from the group consisting of:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated,
(e) a mutated truncated DBP consisting essentially of amino acids 1-211 in which amino acid 76 is mutated, amino acid 79 is mutated, or amino acid 76 and amino acid 79 are mutated,
(f) a mutated truncated DBP consisting essentially of SEQ ID NO:12 in which serine 76 is mutated, serine 79 is mutated, or serine 76 and serine 79 are mutated,
(g) a mutated truncated DBP consisting essentially of SEQ ID NO:2,
(h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6, or
(l) a fusion protein comprising (a), (b), (c), (d), (e), (f), (g), (h), (i), (j), or (k),
whereupon 25-hydroxy vitamin $D_2$ and 25-hydroxy vitamin $D_3$ present in the test sample bind to the DBP, and
(ii) detecting the amount of 25-hydroxy vitamin $D_2$ and 25-hydroxy vitamin $D_3$ bound to DBP, wherein the amount of 25-hydroxy vitamin $D_2$ and 25-hydroxy vitamin $D_3$ bound to DBP is indicative of the total amount of 25-hydroxy vitamin $D_2$ and 25-hydroxy vitamin $D_3$ in the test sample.

Another method of determining the total amount of 25-hydroxy vitamin $D_2$ and 25-hydroxy vitamin $D_3$ in a test sample is also provided. The method comprises:
(i) contacting the test sample with a solid support, which comprises:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated,
(e) a mutated truncated DBP consisting essentially of amino acids 1-211 in which amino acid 76 is mutated, amino acid 79 is mutated, or amino acid 76 and amino acid 79 are mutated,
(f) a mutated truncated DBP consisting essentially of SEQ ID NO:12 in which serine 76 is mutated, serine 79 is mutated, or serine 76 and serine 79 are mutated,
(g) a mutated truncated DBP consisting essentially of SEQ ID NO:2,
(h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6, or
(l) a fusion protein comprising (a), (b), (c), (d), (e), (f), (g), (h), (i), (j), or (k),
whereupon 25-hydroxy vitamin $D_2$ and 25-hydroxy vitamin $D_3$ present in the test sample bind to the solid support,
(ii) optionally separating the solid support and any 25-hydroxy vitamin $D_2$ and 25-hydroxy vitamin $D_3$ that did not bind to the solid support in (i),
(iii) contacting the solid support with a detectably labeled antibody that specifically binds to 25-hydroxy vitamin $D_2$ and 25-hydroxy vitamin $D_3$, wherein the antibody can be a monoclonal antibody, a polyclonal antibody, or an antigenically reactive fragment of an antibody,
(iv) optionally separating the solid support and any detectably labeled antibody that did not bind to 25-hydroxy vitamin $D_2$ and 25-hydroxy vitamin $D_3$ in (iii), and
(v) detecting a signal generated by the detectably labeled antibody and, simultaneously or subsequently, comparing the signal generated by the detectably labeled antibody to a signal generated by a control or calibrator, wherein the signal is directly related to the amount of 25-hydroxy vitamin $D_2$ and 25-hydroxy vitamin $D_3$.

Another method of determining the total amount of 25-hydroxy vitamin $D_2$ and 25-hydroxy vitamin $D_3$ in a test sample is provided. The method comprises:
(i) contacting the test sample with a solid support, which comprises an antibody that specifically binds to 25-hydroxy vitamin $D_2$ and 25-hydroxy vitamin $D_3$, wherein the antibody can be a monoclonal antibody, a polyclonal antibody, or an antigenically reactive fragment of an antibody,
(ii) optionally separating the solid support and any 25-hydroxy vitamin $D_2$ and 25-hydroxy vitamin $D_3$ that did not bind to the solid support in (i),
(iii) contacting the solid support with:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated,
(e) a mutated truncated DBP consisting essentially of amino acids 1-211 in which amino acid 76 is mutated, amino acid 79 is mutated, or amino acid 76 and amino acid 79 are mutated,
(f) a mutated truncated DBP consisting essentially of SEQ ID NO:12 in which serine 76 is mutated, serine 79 is mutated, or serine 76 and serine 79 are mutated,
(g) a mutated truncated DBP consisting essentially of SEQ ID NO:2,
(h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6, or
(l) a fusion protein comprising (a), (b), (c), (d), (e), (f), (g), (h), (i), (j), or (k),
wherein (a)-(l) are detectably labeled,
(iv) optionally separating the solid support and any detectably labeled (a)-(l) that did not bind to 25-hydroxy vitamin $D_2$ and 25-hydroxy vitamin $D_3$ in (iii), and
(v) detecting a signal generated by the detectably labeled (a)-(l) and, simultaneously or subsequently, comparing the signal generated by the detectably labeled (a)-(l) to a signal generated by a control or calibrator, wherein the signal is directly related to the amount of 25-hydroxy vitamin $D_2$ and 25-hydroxy vitamin $D_3$.

Yet another method of determining the total amount of 25-hydroxy vitamin $D_2$ and 25-hydroxy vitamin $D_3$ in a test sample is provided. The method comprises:
(i) contacting the test sample with a DBP, wherein the DBP is selected from the group consisting of:
(a) a truncated DBP consisting essentially of domain I and α-helix 1 of domain II,
(b) a truncated DBP consisting essentially of amino acids 1-211,
(c) a truncated DBP consisting essentially of SEQ ID NO:12,
(d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k), and, simultaneously or sequentially, in either order, contacting the test sample with a specific binding partner for DBP, whereupon 25-hydroxy vitamin $D_2$ and 25-hydroxy vitamin $D_3$ present in the test sample and the specific binding partner for DBP compete for binding to the DBP, and (ii) detecting the amount of specific binding partner bound to DBP, wherein the amount of specific binding partner bound to DBP is indicative of the total amount of 25-hydroxy vitamin $D_2$ and 25-hydroxy vitamin $D_3$ in the test sample.

Still yet another method of determining the total amount of 25-hydroxy vitamin $D_2$ and 25-hydroxy vitamin $D_3$ in a test sample is provided. The method comprises:

(i) contacting a solid support, which comprises:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k), with (i') the test sample and simultaneously or sequentially, in either order, (ii') detectably labeled 25-hydroxy vitamin $D_2$, detectably labeled 25-hydroxy vitamin $D_3$, or detectably labeled 25-hydroxy vitamin $D_2$ and detectably labeled 25-hydroxy vitamin $D_3$, whereupon 25-hydroxy vitamin $D_2$ and 25-hydroxy vitamin $D_3$ present in the test sample and the detectably labeled 25-hydroxy vitamin $D_2$ and/or detectably labeled 25-hydroxy vitamin $D_3$ compete with each other for binding to the solid support, (ii) optionally separating the solid support and any detectably labeled 25-hydroxy vitamin $D_2$ and/or detectably labeled 25-hydroxy vitamin $D_3$ that did not bind to the solid support in (i), and (iii) determining the total amount of 25-hydroxy vitamin $D_2$ and 25-hydroxy vitamin $D_3$ in the test sample based on a signal generated by the detectable label attached to the solid support, wherein the signal generated by the detectable label attached to the solid support is inversely proportional to the total amount of 25-hydroxy vitamin $D_2$ and 25-hydroxy vitamin $D_3$ in the test sample.

Even still yet another method of determining the total amount of 25-hydroxy vitamin $D_2$ and 25-hydroxy vitamin $D_3$ in a test sample is provided. The method comprises:

(i) contacting a solid support, which comprises:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, (l) a fusion protein comprising (a), (b), (c), (d), (e), (f), (g), (h), (i), (j), or (k), or (m) an antibody that specifically binds to 25-hydroxy vitamin $D_2$ and 25-hydroxy vitamin $D_3$, wherein the antibody can be a monoclonal antibody, a polyclonal antibody, or an antigenically reactive fragment of an antibody, wherein (a)-(m) is bound to 25-hydroxy vitamin $D_2$, 25-hydroxy vitamin $D_3$, or 25-hydroxy vitamin $D_2$ and 25-hydroxy vitamin $D_3$, with (i') the test sample and simultaneously or sequentially, in either order, (ii') detectably labeled (m), which is not already bound to 25-hydroxy vitamin $D_2$, 25-hydroxy vitamin $D_3$, or 25-hydroxy vitamin $D_2$ and 25-hydroxy vitamin $D_3$, when the solid support comprises (a), (b), (c), (d), (e), (f), (g), (h), (i), (j), (k), or (l), which is bound to 25-hydroxy vitamin $D_2$, 25-hydroxy vitamin $D_3$, or 25-hydroxy vitamin $D_2$ and 25-hydroxy vitamin $D_3$, or detectably labeled (a), (b), (c), (d), (e), (f), (g), (h), (i), (j), (k), or (l), which is not bound to 25-hydroxy vitamin $D_2$, 25-hydroxy vitamin $D_3$, or 25-hydroxy vitamin $D_2$ and 25-hydroxy vitamin $D_3$, when the solid support comprises (m), which is bound to 25-hydroxy vitamin $D_2$, 25-hydroxy vitamin $D_3$, or 25-hydroxy vitamin $D_2$ and 25-hydroxy vitamin $D_3$, whereupon 25-hydroxy vitamin $D_2$ and 25-hydroxy vitamin $D_3$ present in the test sample and 25-hydroxy vitamin $D_2$ and/or 25-hydroxy vitamin $D_3$ attached to the solid support compete with each other for binding to the detectably labeled (a)-(m) of (ii'), (ii) optionally separating the solid support and any detectably labeled (a)-(m) of (ii') that did not bind to the solid support in (i), and (iii) determining the total amount of 25-hydroxy vitamin $D_2$ and 25-hydroxy vitamin $D_3$ in the test sample based on a signal generated by the detectable label attached to the solid support, wherein the signal generated by the detectable label attached to the solid support is inversely proportional to the total amount of 25-hydroxy vitamin $D_2$ and 25-hydroxy vitamin $D_3$ in the test sample.

BRIEF DESCRIPTION OF THE FIGURES

FIG. 1 is the nucleotide sequence of human vitamin D binding protein truncate 3 (hDBP3) containing the point mutations S76A and S79A (emboldened and italicized) (SEQ ID NO:1).

FIG. 2 is the amino acid sequence of hDBP3 containing the point mutations S76A and S79A (emboldened and italicized) (SEQ ID NO:2).

FIG. 3 is the nucleotide sequence encoding the additional amino acid sequence present in hDBP truncate 4 (hDBP4) (SEQ ID NO:3).

FIG. 4 is the additional amino acid sequence present in hDBP4 (SEQ ID NO:4).

FIG. 5 is the nucleotide sequence of hDBP3 containing the point mutations S76A and S79A (emboldened and italicized) fused to the additional 56 amino acids present in hDBP4 (SEQ ID NO:5).

FIG. 6 is the amino acid sequence of hDBP3 containing the point mutations S76A and S79A (emboldened and italicized) fused to the additional 56 amino acids present in hDBP4 (SEQ ID NO:6).

FIG. 7 is the nucleotide sequence of human IgG Fc less the first six amino acids (SEQ ID NO:7).

FIG. 8 is the amino acid sequence of human IgG Fc less the first six amino acids (SEQ ID NO:8).

FIG. 9 is the nucleotide sequence of hDBP3 containing the point mutations S76A and S79A (emboldened and italicized) fused to the additional 56 amino acids present in hDBP4 and human IgG Fc less the first six amino acids (SEQ ID NO:9).

FIG. 10 is the amino acid sequence of hDBP3 containing the point mutations S76A and S79A (emboldened and italicized) fused to the additional 56 amino acids present in hDBP4 and human IgG Fc less the first six amino acids (SEQ ID NO:10).

FIG. 11 is the nucleotide sequence of wild-type hDBP3 (SEQ ID NO:11) containing the wild-type sequence. The sequence is emboldened and italicized at positions where S76A and S79A mutations have been introduced for mutant sequences described herein.

FIG. 12 is the amino acid sequence of wild-type hDBP3 (SEQ ID NO:12). The sequence is emboldened and italicized at positions where S76A and S79A mutations have been introduced for mutant sequences described herein.

FIG. 13 is the nucleotide sequence of wild-type hDBP4 (SEQ ID NO:13), wherein the nucleotide sequence encoding the additional 56 amino acids is underlined. The sequence furthermore is emboldened and italicized at positions where S76A and S79A mutations have been introduced for mutant sequences described herein.

FIG. 14 is the amino acid sequence of wild-type hDBP4 (SEQ ID NO:14), wherein the additional 56 amino acids are underlined. The sequence furthermore is emboldened and italicized at positions where S76A and S79A mutations have been introduced for mutant sequences described herein.

DETAILED DESCRIPTION

Figure 15:
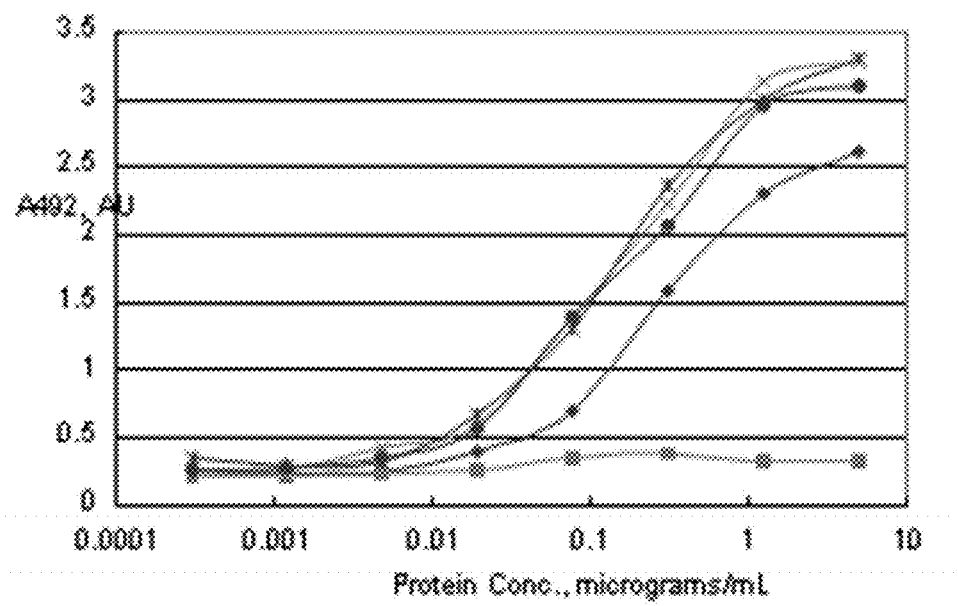
FIG. 15 is a graph showing the activity enzyme immunoassay of hDBP4-hFc 3-6. Symbols: triangle, wild-type hDBP4; square, negative control; 'x', hDBP4-hFc 3-6 protein expressed from Human Embryonic Kidney (HEK), orbital shaker used for growing cells; '*', hDBP4-hFc 3-6 protein expressed from HEK cells, Wave Bag™ used for growing cells; circle, hDBP4-hFc 3-6 protein expressed from Chinese Hamster Ovary (CHO).

The present disclosure is predicated, at least in part, on the discovery of a truncated vitamin D binding protein (DBP) and a mutated truncated DBP. In view of the foregoing, fusion proteins, nucleic acid molecules, vectors, host cells, and methods, kits and solid supports for determining the total amount of vitamin D, specifically 25-hydroxy vitamin $D_2$ and 25-hydroxy vitamin $D_3$, in a test sample are provided.

Definitions

The following terms are relevant to the present disclosure:

"About" refers to approximately a +/−10% variation from the stated value. It is to be understood that such a variation is always included in any given value provided herein, whether or not specific reference is made to it.

"Antibody" and "antibodies" refer to monoclonal antibodies, multispecific antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass. An antibody, whose affinity (namely, $K_D$, $k_d$ or $k_a$) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody," or merely an "analyte antibody" (e.g., an anti-vitamin D antibody or a vitamin D antibody).

"Antibody fragment," "antigenically reactive fragment of an antibody," and "antibody fragments" refer to a portion of an intact antibody comprising the antigen-binding site or variable region. The portion does not include the constant heavy chain domains (i.e., $CH_2$, $CH_3$ or $CH_4$, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Component," "components," and "at least one component," refer generally to a capture antibody, a detection or conjugate antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

"Control" refers to a composition known to not contain an analyte of interest, such as, in the context of the present disclosure, vitamin D, specifically 25-hydroxy vitamin D$_2$ and/or 25-hydroxy vitamin D$_3$ ("negative control"), or to contain an analyte of interest, such as, in the context of the present disclosure, vitamin D, specifically 25-hydroxy vitamin D$_2$ and/or 25-hydroxy vitamin D$_3$ ("positive control"). A positive control can comprise a known concentration of vitamin D, specifically 25-hydroxy vitamin D$_2$ and/or 25-hydroxy vitamin D$_3$. "Control," "positive control," and "calibrator" may be used interchangeably herein to refer to a composition comprising a known concentration of vitamin D, specifically 25-hydroxy vitamin D$_2$ and/or 25-hydroxy vitamin D$_3$. A "positive control" can be used to establish assay performance characteristics and is a useful indicator of the integrity of reagents (e.g., analytes).

"Cross-reactivity" refers to the ability of an antigen-binding site of an antibody to react with more than one antigen. Cross-reactivity occurs when an antigen has an epitope that is identical to an epitope on the antigen to which the antibody was generated (oftentimes referred to as an "immunizing antigen"). Cross-reactivity also occurs when an antigen has an epitope that is structurally similar, but not identical, to an epitope on the antigen to which the antibody was generated. In the context of the present disclosure, an antibody, such as an antibody used in the context of an assay (e.g., immunoassay), which binds to 25-hydroxy vitamin D$_2$ and 25-hydroxy vitamin D$_3$, preferably specifically binds to 25-hydroxy vitamin D$_2$ and 25-hydroxy vitamin D$_3$. Such an antibody, however, may cross-react with 1,25-hydroxy vitamin D$_2$ and 25-hydroxy vitamin D$_3$ and still be useful in the context of an assay, such as an immunoassay, as described herein. Similarly, a vitamin D binding protein (DBP (e.g., truncated, mutated truncated, or fusion protein of either of the foregoing)), which binds to 25-hydroxy vitamin D$_2$ and 25-hydroxy vitamin D$_3$, preferably specifically binds to 25-hydroxy vitamin D$_2$ and 25-hydroxy vitamin D$_3$. Such a DBP, however, may cross-react with 1,25-hydroxy vitamin D$_2$ and 25-hydroxy vitamin D$_3$ and still be useful in the context of an assay, such as an immunoassay, as described herein.

"Epitope," "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Label" and "detectable label" mean a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6×His tag, which has an amino acid sequence of HHHHHH (SEQ ID NO:15), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:16) and derivatives thereof (e.g., ADDDDK (SEQ ID NO:17), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human at risk for rickets, hypocalcemia, hypercalcemia, or osteomalcia.

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels. However, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., vitamin D) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multivalent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Risk" refers to the possibility or probability of a particular event occurring either presently, or, at some point in the future. "Risk stratification" refers to an array of known clinical risk factors that allows physicians to classify patients into a low, moderate, high or highest risk of developing a particular disease, disorder or condition.

"Sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. In the context of the present disclosure, the sample is preferably serum or plasma.

"Series of calibrating compositions" refers to a plurality of compositions comprising a known concentration of an analyte of interest, such as vitamin D, specifically 25-hydroxy vitamin $D_2$ and/or 25-hydroxy vitamin $D_3$, wherein each of the compositions differs from the other compositions in the series by the concentration of the analyte of interest.

"Solid phase" or "solid support" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Specific" and "specificity" in the context of an interaction between members of a specific binding pair (e.g., an antigen (or a fragment thereof) and an antibody (or antigenically reactive fragment thereof), and a binding protein (or a fragment thereof) and its ligand, such as the vitamin D binding proteins (DBPs) and their ligands as described herein) refer to the selective reactivity of the interaction. The phrase "specifically binds to" and analogous phrases refer to the ability of antibodies (or antigenically reactive fragments thereof) to bind specifically to an antigen, such as vitamin D (or a fragment thereof), and not bind specifically to other antigens (or fragments thereof). The phrase "specifically binds to" and analogous phrases also refers to the ability of hDBPs (or antigenically reactive fragments thereof) to bind specifically to an antigen, such as 25-hydroxy vitamin D (or a fragment thereof), and not bind specifically to other antigens (or fragments thereof).

Generally, specific binding is measured by means of "binding constants," as described herein. The term "association rate constant," "$k_{on}$," or "$k_a$" as used herein, refers to the value indicating the binding rate, or the rate of complex formation, of the first member of a specific binding pair (for example, an antibody of an antibody-antigen specific binding pair or a DBP (e.g., truncated, mutated truncated, or fusion protein of either of the foregoing) of a DBP-vitamin D specific binding pair) to the second member of a specific binding pair (for example, an antigen of an antibody-antigen specific binding pair or a vitamin D of a DBP-vitamin D specific binding pair) as shown by the equation below:

first member of specific binding pair ($A$)+second member of specific binding pair ($B$)→$A$-$B$.

The term "dissociation rate constant," "$k_{off}$" or "$k_d$" as used interchangeably herein, refers to the value indicating the dissociation rate, or the rate of complex separation, of the first member of a specific binding pair (for example, an antibody of an antibody-antigen specific binding pair or a DBP (e.g., truncated, mutated truncated, or fusion protein of either of the foregoing) of a DBP-vitamin D specific binding pair) from the second member of a specific binding pair (for example, an antigen of an antibody-antigen specific binding pair or a vitamin D of a DBP-vitamin D specific binding pair) as shown by the equation below:

first member of specific binding pair ($A$)+second member of specific binding pair←$A$-$B$.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

"Substantially identical" as used herein means that a first sequence and a second sequence are at least from about 50% to about 99% identical over a region from about 8 to about 100 or more residues (including, in particular, any range from about 8 to about 100 residues).

"Tracer" means an analyte or analyte fragment conjugated to a label, such as vitamin D conjugated to a fluorescein moiety, wherein the analyte conjugated to the label can effectively compete with the analyte for sites on an antibody specific for the analyte.

"Variant" as used herein means a polypeptide that differs from a given polypeptide (i.e., vitamin D binding protein) in amino acid sequence by the insertion, deletion, or conservative substitution of amino acids, but that retains the biological activity of the given polypeptide (i.e., can compete with vitamin D binding protein as defined herein for binding to vitamin D, such as 25-hydroxy vitamin $D_2$ and/or 25-hydroxy vitamin $D_3$). A conservative substitution of an amino acid, i.e., replacing an amino acid with a different amino acid of similar properties (e.g., hydrophilicity and degree and distribution of charged regions), is recognized in the art as typically involving a minor change. These minor changes can be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group. "Variant" also can be used to refer to an antigenically reactive fragment of an anti-vitamin D antibody that differs from the corresponding fragment of anti-vitamin D antibody in amino acid sequence but is still antigenically reactive and can compete with the corresponding fragment of anti-vitamin D antibody for binding with vitamin D. "Variant" also can be used to describe a polypeptide or a fragment thereof that has been differentially processed, such as by proteolysis, phosphorylation, or other post-translational modification, yet retains its antigen reactivity, i.e., ability to bind to vitamin D, has been fused with another compound, e.g., polyethylene glycol, to increase its half-life, or has been modified by the addition of a leader, signal or secretory sequence or a sequence employed for purification.

The above terminology is provided for the purpose of describing particular embodiments. The terminology is not intended to be limiting.

Truncated Vitamin D Binding Protein and Mutations and Fusions Thereof

A truncated vitamin D binding protein (DBP) consisting essentially of domain I and α-helix 1 of domain II is provided. The truncated DBP can consist essentially of amino acids 1-211. The truncated DBP can consist essentially of SEQ ID NO:12.

A mutated truncated DBP consisting essentially of domain I and α-helix 1 of domain II in which amino acid 76 is mutated, amino acid 79 is mutated, or amino acid 76 and amino acid 79 are mutated is provided. The mutated truncated DBP can consist essentially of amino acids 1-211 in which amino acid 76 is mutated, amino acid 79 is mutated, or amino acid 76 and amino acid 79 are mutated. The mutated truncated DBP can consist essentially of SEQ ID NO:12 in which serine 76 is mutated, serine 79 is mutated, or serine 76 and serine 79 are mutated. The mutated truncated DBP can consist essentially of SEQ ID NO:2.

A mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated is also provided. The mutated truncated DBP can consist essentially of amino acids 1-267 in which amino acid 76 is mutated, amino acid 79 is mutated, or amino acid 76 and amino acid 79 are mutated. The mutated truncated DBP can consist essentially of SEQ ID NO:14 in which serine 76 is mutated, serine 79 is mutated, or serine 76 and serine 79 are mutated. The mutated truncated DBP can consist essentially of SEQ ID NO:6.

Amino acids in the truncated DBP that are essential for function can be identified by methods known in the art, e.g., site-directed mutagenesis or alanine-scanning mutagenesis. The latter procedure introduces single alanine mutations at every residue in the molecule, and the resulting mutant molecules are test for biological activity. Sites that are critical for binding to vitamin D, specifically 25-hydroxy vitamin $D_2$ and 25-hydroxy vitamin $D_3$, also can be determined by structural analysis, such as crystallization. Similarly, functional variants can be developed using nuclear magnetic resonance or photoaffinity labeling. Such techniques can be used to identify other mutations, such as conservative amino acid substitutions, that can be introduced into the mutated truncated DBP.

Also provided is a fusion protein comprising (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, or (k) a mutated truncated DBP consisting essentially of SEQ ID NO:6. The fusion protein can further comprise a human IgG1 constant fragment (hFc). The fusion protein can comprise the amino acid sequence of SEQ ID NO:10.

A truncated (DBP), a mutated truncated DBP, or a fusion protein of either of the foregoing, which binds to 25-hydroxy vitamin $D_2$ and 25-hydroxy vitamin $D_3$, preferably specifically (or preferentially) binds to 25-hydroxy vitamin $D_2$ and 25-hydroxy vitamin $D_3$, optionally with similar reactivity, such as with equimolar affinity. Such a truncated DBP, mutated truncated DBP, or fusion protein thereof, however, may cross-react (see, e.g., discussion of "cross-reactivity" herein above) with 1,25-hydroxy vitamin $D_2$ and 25-hydroxy vitamin $D_3$ and still be useful in the context of an assay, such as an immunoassay, as described herein.

Synthetic Production

Once sequenced, polypeptides, such as a truncated DBP or a mutated truncated DBP, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Hely. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also described by Stewart and Young in Solid Phase Peptide Syntheses (2nd Ed., Pierce Chemical Company, 1984).

Recombinant Production

A polypeptide, such as a truncated DBP or a mutated truncated DBP, can be recombinantly produced using methods known in the art. For example, an isolated or purified nucleic acid molecule comprising a nucleotide sequence encoding the polypeptide can be expressed in a host cell, and the polypeptide can be isolated. The isolated or purified nucleic acid molecule can comprise a nucleotide sequence encoding (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, or (k) a mutated truncated DBP consisting essentially of SEQ ID NO:6. The isolated or purified nucleic acid molecule can comprise the nucleotide sequence of SEQ ID NO:11, SEQ ID NO:1, or SEQ ID NO:5. The isolated or purified nucleic acid molecule can comprise a nucleotide sequence encoding a fusion protein of a truncated DBP or a mutated truncated DBP as described above, in which case the isolated or purified nucleic acid molecule can comprise the nucleotide sequence of SEQ ID NO:9. The isolated or purified nucleic acid molecule can be a vector.

The isolated nucleic acid can be synthesized with an oligonucleotide synthesizer, for example. One of ordinary skill in the art will readily appreciate that, due to the degeneracy of the genetic code, more than one nucleotide sequence can encode a given amino acid sequence. In this regard, a nucleotide sequence encoding an amino acid sequence that is substantially identical to an amino acid sequence of a SEQ ID NO specified herein can be used, provided that the variant truncated DBP or variant mutated truncated DBP as expressed competes with the truncated DBP or mutated truncated DBP, respectively, comprising the amino acid sequence of the specified SEQ ID NO for binding to vitamin D, specifically 25-hydroxy vitamin $D_2$ and/or 25-hydroxy vitamin $D_3$. Codons, which are favored by a given host cell, preferably are selected for recombinant production. A nucleotide sequence encoding the amino acid sequence of a specified SEQ ID NO can be combined with other nucleotide sequences using polymerase chain reaction (PCR), ligation, or ligation chain reaction (LCR) to encode a mutated truncated DBP. The individual oligonucleotides typically contain 5' or 3' overhangs for complementary assembly. Once assembled, the nucleotide sequence encoding a truncated DBP or a mutated truncated DBP can be inserted into a vector, operably linked to control sequences as necessary for expression in a given host cell, and introduced (such as by transformation or transfection) into a host cell. The nucleotide sequence can be further manipulated (for example, linked to one or more nucleotide sequences encoding additional immunoglobulin domains, such as additional constant regions) and/or expressed in a host cell.

Although not all vectors and expression control sequences may function equally well to express a polynucleotide sequence of interest and not all hosts function equally well with the same expression system, it is believed that those skilled in the art will be able to make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors also can be considered. These include, but are not limited to, the relative strength of the sequence, its controllability, and its compatibility with the nucleotide sequence encoding the truncated DBP, mutated truncated DBP, or fusion protein of either of the foregoing, particularly with regard to potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products encoded by the nucleotide sequence, etc.

The recombinant vector can be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector in which the polynucleotide sequence encoding the truncated DBP, mutated truncated DBP, or fusion protein of either of the foregoing, is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include pcDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2 μ plasmid and derivatives thereof, the POT1 vector (see, e.g., U.S. Pat. No. 4,931,373), the pJSO37 vector (described in Okkels, Ann New York Acad. Sci. 782: 202-207 (1996)) and pPICZ A, B or C (Invitrogen). Examples of expression vectors for use in insect cells include, but are not limited to, pVL941, pBG311 (Cate et al., Cell 45: 685-698 (1986)), and pBluebac 4.5 and pMelbac (both of which are available from Invitrogen).

Other vectors that can be used allow the nucleotide sequence encoding the truncated DBP, mutated truncated DBP, or fusion protein of either of the foregoing, to be amplified in copy number. Such amplifiable vectors are well-known in the art. These vectors include, but are not limited to, those vectors that can be amplified by dihydrofolate reductase (DHFR) amplification (see, for example, Kaufinan, U.S. Pat. No. 4,470,461; and Kaufinan et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector can further comprise a nucleotide sequence enabling the vector to replicate in the host cell in question. An example of such a sequence for use in a mammalian host cell is the SV40 origin of replication. Suitable sequences enabling the vector to replicate in a yeast cell are the yeast plasmid 2μ replication genes REP 1-3 and origin of replication.

The vector can also comprise a selectable marker, namely, a gene or polynucleotide, the product of which complements a defect in the host cell, such as the gene coding for DHFR or the *Schizosaccharomyces pombe* TPI gene (see, e.g., Russell, Gene 40: 125-130 (1985)), or one which confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

Also present in the vector are "control sequences," which are any components that are necessary or advantageous for the expression of the truncated DBP, mutated truncated DBP, or fusion protein of either of the foregoing. Each control sequence can be native or foreign to the nucleotide sequence encoding the truncated DBP, mutated truncated DBP, or fusion protein of either of the foregoing. Such control sequences include, but are not limited to, a leader, a polyadenylation sequence, a propeptide sequence, a promoter, an enhancer or an upstream activating sequence, a signal peptide sequence, and a transcription terminator. At a minimum, the control sequences include at least one promoter operably linked to the polynucleotide sequence encoding the truncated DBP, mutated truncated DBP, or fusion protein of either of the foregoing.

By "operably linked" is meant the covalent joining of two or more nucleotide sequences, by means of enzymatic ligation or otherwise, in a configuration relative to one another such that the normal function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in the same reading frame. Linking is accomplished by ligation at convenient restriction sites. If such sites do not exist, then synthetic oligonucleotide adaptors or linkers can be used, in conjunction with standard recombinant DNA methods.

A wide variety of expression control sequences can be used in the context of the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, J. Mol. Biol. 196: 947-50 (1987)).

In order to improve expression in mammalian cells a synthetic intron can be inserted in the 5' untranslated region of a polynucleotide sequence encoding the antibody or a fragment thereof. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter, the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator, and the ADH3 terminator.

The polynucleotide sequence encoding the truncated DBP, mutated truncated DBP, or fusion protein of either of the foregoing may or may not also include a polynucleotide sequence that encodes a signal peptide. The signal peptide is present when the truncated DBP (or fusion protein thereof) or mutated truncated DBP (or fusion protein thereof) is to be secreted from the cells in which it is expressed. Such signal peptide, if present, should be one recognized by the cell chosen for expression of the polypeptide. The signal peptide can be homologous or heterologous to the truncated DBP (or fusion protein thereof) or mutated truncated DBP (or fusion protein thereof) or can be homologous or heterologous to the host cell, i.e., a signal peptide normally expressed from the host cell or one which is not normally expressed from the host cell. Accordingly, the signal peptide can be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the truncated DBP (or fusion protein thereof) or mutated truncated DBP (or fusion protein thereof). For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide can be derived from an insect gene (see, e.g., Int'l Pat. App. Pub. No. WO 90/05783), such as the lepidopteran *Manduca sexta* adipokinetic hormone precursor (see, e.g., U.S. Pat. No. 5,023,328), the honeybee melittin (Invitrogen), ecdysteroid UDP glucosyltransferase (egt) (Murphy et al., Protein Expression and Purification 4: 349-357 (1993), or human pancreatic lipase (hpl) (Methods in Enzymology 284: 262-272 (1997)).

Specific examples of signal peptides for use in mammalian cells include murine Ig kappa light chain signal peptide (Coloma, J. Imm Methods 152: 89-104 (1992)). Suitable signal peptides for use in yeast cells include the α-factor signal peptide from *S. cerevisiae* (see, e.g., U.S. Pat. No. 4,870,008), the signal peptide of mouse salivary amylase (see, e.g., Hagenbuchle et al., Nature 289: 643-646 (1981)), a modified carboxypeptidase signal peptide (see, e.g., Valls et al., Cell 48: 887-897 (1987)), the yeast BAR1 signal peptide (see, e.g., Int'l Pat. App. Pub. No. WO 87/02670), and the yeast aspartic protease 3 (YAPS) signal peptide (see, e.g., Egel-Mitani et al., Yeast 6: 127-137 (1990)).

In view of the above, the above-described isolated or purified nucleic acid molecule, which can be a vector, can be introduced into a host cell as described herein below. Accordingly, a host cell comprising the isolated or purified nucleic acid molecule is provided.

Any suitable host can be used to produce the truncated DBP or mutated truncated DBP, including bacteria, fungi (including yeasts), plant, insect, mammal or other appropriate animal cells or cell lines, as well as transgenic animals or plants. A preferred host cell is a Chinese hamster ovary (CHO) cell. Examples of bacterial host cells include, but are not limited to, gram-positive bacteria, such as strains of *Bacillus*, for example, *B. brevis* or *B. subtilis*, *Pseudomonas* or *Streptomyces*, or gram-negative bacteria, such as strains of *E. coli*. The introduction of a vector into a bacterial host cell can, for instance, be effected by protoplast transformation (see, for example, Chang et al., Molec. Gen. Genet. 168: 111-115 (1979)), using competent cells (see, for example, Young et al., J. of Bacteriology 81: 823-829 (1961), or Dubnau et al., J. of Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae*, *A. niger*, or *A. nidulans*, *Fusarium* or *Trichoderma*. Fungal cells can be transformed by a process involving protoplast formation, transformation of the protoplasts, and regeneration of the cell wall using techniques known to those ordinarily skilled in the art. Suitable procedures for transformation of *Aspergillus* host cells are described in European Pat. App. Pub. No. 238 023 and U.S. Pat. No. 5,679,543. Suitable methods for transforming *Fusarium* species are described by Malardier et al., Gene 78: 147-156 (1989), and Int'l Pat. App. Pub. No. WO 96/00787. Yeast can be transformed using the procedures described by Becker and Guarente, In Abelson, J. N. and Simon, M. I., editors, *Guide to Yeast Genetics and Molecular Biology*, Methods in Enzymology 194: 182-187, Academic Press, Inc., New York; Ito et al, J. of Bacteriology 153: 163 (1983); and Hinnen et al., PNAS USA 75: 1920 (1978).

Examples of suitable yeast host cells include strains of *Saccharomyces*, for example, *S. cerevisiae, Schizosaccharomyces, Klyveromyces, Pichia*, such as *P. pastoris* or *P. methanolica, Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99: 193-198 (1992), Manivasakam et al., Nucleic Acids Research 21: 4414-4415 (1993), and Ganeva et al., FEMS Microbiology Letters 121: 159-164 (1994).

Examples of suitable insect host cells include, but are not limited to, a *Lepidoptora* cell line, such as *Spodoptera frugiperda* (Sf9 or Sf21) or *Trichoplusia ni* cells (High Five) (see, e.g., U.S. Pat. No. 5,077,214). Transformation of insect cells and production of heterologous polypeptides are well-known to those skilled in the art.

Examples of suitable mammalian host cells include Chinese hamster ovary (CHO) cell lines, simian (e.g., Green Monkey) cell lines (COS), mouse cells (for example, NS/O), baby hamster kidney (BHK) cell lines, human cells (such as human embryonic kidney (HEK) cells (e.g., HEK 293 cells (A.T.C.C. Accession No. CRL-1573)), myeloma cells that do not otherwise produce immunoglobulin protein, and plant cells in tissue culture. Preferably, the mammalian host cells are CHO cell lines and HEK 293 cell lines. Another preferred host cell is the B3.2 cell line (e.g., Abbott Laboratories, Abbott Bioresearch Center, Worcester, Mass.), or another dihydrofolate reductase deficient (DHFR$^-$) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well-known in the art and are described, for example, by Ausbel et al. (eds.), *Current Protocols in Molecular Biology*, John Wiley & Sons, New York, USA (1996). The cultivation of mammalian cells is conducted according to established methods, e.g., as disclosed in Jenkins, Ed., *Animal Cell Biotechnology, Methods and Protocols*, Human Press Inc. Totowa, N.J., USA (1999), and Harrison and Rae, *General Techniques of Cell Culture*, Cambridge University Press (1997).

In the production methods, cells are cultivated in a nutrient medium suitable for production of the truncated DBP (or fusion protein thereof) or mutated truncated DBP (or fusion protein thereof) using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the truncated DBP (or fusion protein thereof) or mutated truncated DBP (or fusion protein thereof) to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the truncated DBP (or fusion protein thereof) or mutated truncated DBP (or fusion protein thereof) is secreted into the nutrient medium, it can be recovered directly from the medium. If the truncated DBP (or fusion protein thereof) or mutated truncated DBP (or fusion protein thereof) is not secreted, it can be recovered from cell lysates.

The resulting truncated DBP (or fusion protein thereof) or mutated truncated DBP (or fusion protein thereof) can be recovered by methods known in the art. For example, the truncated DBP (or fusion protein thereof) or mutated truncated DBP (or fusion protein thereof) can be recovered from the nutrient medium by conventional procedures including, but not limited to, centrifugation, filtration, extraction, spray drying, evaporation, or precipitation.

The truncated DBP (or fusion protein thereof) or mutated truncated DBP (or fusion protein thereof) can be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, *Protein Purification*, VCH Publishers, New York (1989)).

Anti-Vitamin D Antibody

An anti-vitamin D antibody can be used in the context of the methods and kits disclosed herein. The antibody can be a monoclonal or polyclonal antibody or an antigenically reactive fragment thereof. Preferably, the anti-vitamin D antibody binds to vitamin D, specifically 25-hydroxy vitamin $D_2$ and/or 25-hydroxy vitamin $D_3$ (collectively, 25-hydroxy vitamin D) at a site that is not bound by a DBP, specifically a truncated DBP or a mutated truncated DBP (or a variant or fusion protein of either of the foregoing).

An antibody (or antigenically reactive fragment thereof) that specifically binds to vitamin D, specifically 25-hydroxy vitamin $D_2$ and/or 25-hydroxy vitamin $D_3$, can be made using a variety of different techniques known in the art. For example, polyclonal and monoclonal antibodies can be raised by immunizing a suitable subject (such as, but not limited to, a rabbit, a goat, a mouse, or other mammal) with an immunogenic preparation, which contains a suitable immunogen. The immunogen can be enriched/purified and isolated from a cell that produces it using affinity chromatography, immune-precipitation or other techniques, which are well-known in the art. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof).

The unit dose of immunogen (namely, the purified protein, tumor cell expressing the protein, or recombinantly expressed immunogen (or a fragment or a variant (or a fragment thereof) thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Int'l Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody-producing cells can be harvested from an immunized animal and used to prepare monoclonal antibodies using standard techniques. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the Epstein-Barr virus (EBV)-hybridoma technique to produce human monoclonal antibodies (Cole et al., *Monoclonal Antibodies and Cancer Therapy*, Alan R. Liss, Inc. pp. 77-96 (1985)). The technology for producing monoclonal antibody hybridomas is well-known to those skilled in the art.

Monoclonal antibodies also can be made by harvesting antibody-producing cells, for example, splenocytes, from transgenic mice, which express human immunoglobulin genes and which have been immunized with the immunogen. The splenocytes can be immortalized through fusion with human myelomas or through transformation with EBV. These hybridomas can be made using human B cell- or EBV-hybridoma techniques described in the art (See, for example, Boyle et al., European Pat. Pub. No. 0 614 984).

Hybridoma cells producing a monoclonal antibody, which specifically binds to the immunogen, are detected by screening the hybridoma culture supernatants by, for example, screening to select antibodies that specifically bind to the immobilized immunogen (or a fragment thereof), or by testing the antibodies as described herein to determine if the antibodies have the desired characteristics, namely, the ability to bind to immunogen (or a fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in *Monoclonal Antibodies: A New Dimension In Biological Analyses*, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD 1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Once a monoclonal antibody that specifically binds to vitamin D, specifically 25-hydroxy vitamin $D_2$ and/or 25-hydroxy vitamin $D_3$, is obtained in accordance with methods described above, it can be sequenced in accordance with methods known in the art. The antibody then can be made using recombinant DNA technology, chemical synthesis, or a combination of chemical synthesis and recombinant DNA technology as described above.

Furthermore, in some aspects of the disclosure, it may be possible to employ commercially available anti-vitamin D antibodies. There are a number of polyclonal and monoclonal antibodies available from various vendors. Alternatively, anti-vitamin D antibodies can be produced using methods described in the literature.

An antigenically reactive fragment of an antibody that binds to vitamin D, specifically 25-hydroxy vitamin $D_2$ and/or 25-hydroxy vitamin $D_3$, also can be used. The antibody fragment can be a Fab, a Fab', a Fab'-SH fragment, a di-sulfide linked Fv, a single chain Fv (scFv), a $F(ab')_2$ fragment, and the like. Various techniques are known to those skilled in the art for the production of antibody fragments. For example, such fragments can be derived via proteolytic digestion of intact antibodies (see, for example, Morimoto et al., J. Biochem. Biophys. Methods 24: 107-117 (1992), and Brennan et al., Science 229: 81 (1985)) or produced directly by recombinant host cells. For example, Fab'-SH fragments can be directly recovered from *E. coli* and chemically coupled to form $F(ab')_2$ fragments (see, e.g., Carter et al., Bio/Technology 10: 163-167 (1992)). In another embodiment, the $F(ab')_2$ is formed using the leucine zipper GCN4 to promote assembly of the $F(ab')_2$ molecule. Alternatively, Fv, Fab or $F(ab')_2$ fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)). The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art. Moreover, other forms of single-chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or a fragment thereof) can be used as one or more immunodiagnostic reagents. For example, the antibodies can be used as one or more immunodiagnostic reagents in one or more methods for detecting the presence of vitamin D, specifically 25-hydroxy vitamin $D_2$ and/or 25-hydroxy vitamin $D_3$, in a test sample. More specifically, the antibody (or antigenically reactive fragment thereof) can be used as a capture antibody or a detection antibody in an immunoassay to detect the presence of vitamin D, specifically 25-hydroxy vitamin $D_2$ and/or 25-hydroxy vitamin $D_3$, in a test sample.

Solid Support

Also provided is a solid support to which is attached:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k).

The fusion protein can comprise a human IgG1 constant fragment (hFc). The fusion protein can comprise the amino acid sequence of SEQ ID NO:10. Any of (a)-(k) can be attached to the solid support by an anti-DBP antibody or (l) can be attached to the solid support by either of an anti-DBP antibody or an antibody that binds to a protein to which any of (a)-(k) is fused to form the fusion protein of (l).

The solid support can be any suitable solid support as known in the art. For example, the solid support can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

The truncated DBP (or fusion protein thereof) or mutated truncated DBP (or fusion protein thereof) can be attached to the solid support as a capture agent using any suitable method as known in the art. For example, a solid support can be chosen because it has an intrinsic ability to attract and immobilize a capture agent. Alternatively, the solid support can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid support and that has the ability to immobilize the capture agent through a binding reaction. The linking agent enables the indirect binding of the capture agent to a solid support material before the performance of the assay or during the performance of the assay.

Kit

A kit for assay of 25-hydroxy vitamin $D_2$ and 25-hydroxy vitamin $D_3$ is also provided. The kit comprises at least one component for assaying the test sample for vitamin D, specifically 25-hydroxy vitamin $D_2$ and 25-hydroxy vitamin $D_3$, and instructions for assaying the test sample for 25-hydroxy vitamin $D_2$ and 25-hydroxy vitamin $D_3$. Thus, the kit comprises:

(i) instructions for assaying a test sample for 25-hydroxy vitamin $D_2$ and 25-hydroxy vitamin $D_3$ and (ii) one or more of:

(a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, (l) a fusion protein comprising (a), (b), (c), (d), (e), (f), (g), (h), (i), (j), or (k), and (m) a solid support comprising (a), (b), (c), (d), (e), (f), (g), (h), (i), (j), (k), or (l), wherein any of (a)-(m) can be detectably labeled. Any of (a)-(k) can be attached to the solid support of (m) by an anti-DBP antibody or (l) can be attached to the solid support of (m) by either of an anti-DBP antibody or an antibody that binds to a protein to which any of (a)-(k) is fused to form the fusion protein of (l).

For example, the kit can comprise instructions for assaying the test sample for vitamin D, specifically 25-hydroxy vitamin $D_2$ and 25-hydroxy vitamin $D_3$, by immunoassay, e.g., chemiluminescent microparticle immunoassay. The instructions can be in paper form or computer-readable form, such as a disk, CD, DVD, or the like. The kit can comprise an antibody for assaying the test sample. For example, the antibody can be a vitamin D capture antibody or a vitamin D detection antibody. The DBPs alone or combined with anti-vitamin D antibodies alternately can be employed in clinical chemistry format such as would be known by one skilled in the art. Alternatively or additionally, the kit can comprise a calibrator or control, e.g., purified, and optionally lyophilized, vitamin D, and/or at least one container (e.g., tube, microtiter plates or strips, which can be already coated with an anti-vitamin D monoclonal antibody, truncated DBP, or mutated truncated DBP) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying vitamin D, specifically 25-hydroxy vitamin $D_2$ and 25-hydroxy vitamin $D_3$.

Any truncated DBP (or fusion protein thereof), mutated truncated DBP (or fusion protein thereof), or anti-vitamin D antibody, which is provided in the kit, can incorporate a detectable label, such as a fluorophore, radioactive moiety, enzyme, biotin/avidin label, chromophore, chemiluminescent label, or the like, or the kit can include reagents for labeling the truncated DBP (or fusion protein thereof), mutated truncated DBP (or fusion protein thereof), or anti-vitamin D antibody for detecting vitamin D. The truncated DBP (or fusion protein thereof), mutated truncated DBP (or fusion protein thereof), anti-vitamin D antibody, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc or chip.

Methods of Determining the Presence, Amount or Concentration of 25-Hydroxy Vitamin $D_2$ and 25-Hydroxy Vitamin $D_3$ (or a Fragment Thereof)

Methods for determining the presence, total amount, or concentration of vitamin D, specifically 25-hydroxy vitamin $D_2$ and 25-hydroxy vitamin $D_3$ (collectively, 25-hydroxy vitamin D), or fragments thereof, in a test sample are provided. Any suitable assay as is known in the art can be used in the method. Examples include, but are not limited to, immunoassay, such as sandwich immunoassay (e.g., monoclonal-polyclonal sandwich immunoassays or antibody-vitamin D binding protein (DBP), including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds (e.g., an antibody that specifically binds 25-hydroxy vitamin $D_2$ and 25-hydroxy vitamin $D_3$, such as one provided herein, or a DBP) is attached to the surface of a mass spectrometry probe, such as a pre-activated protein chip array. The vitamins 25-hydroxy vitamin $D_2$ and 25-hydroxy vitamin $D_3$ (or fragments thereof) are then specifically captured on the biochip, and the captured 25-hydroxy vitamin $D_2$ and 25-hydroxy vitamin $D_3$ (or fragments thereof) of interest are detected by mass spectrometry. Alternatively, the 25-hydroxy vitamin $D_2$ and 25-hydroxy vitamin $D_3$ (or fragments thereof) can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay.

Clinical chemistry also can be used in the context of the present disclosure. Clinical chemistry involves the analysis of bodily fluids, such as blood, urine, cerebrospinal fluid (CSF), effusions, as well as feces, or components of any of the foregoing, by various techniques ranging from simple chemical analysis (e.g., liver function and kidney function), to the use and measurement of enzymatic activity, spectrophotometry, and electrophoresis. Clinical chemistry also includes endocrinology, toxicology, and therapeutic drug monitoring. Clinical chemistry furthermore may include use of only a single antibody, turbidimetric assays, and particle-enhanced turbidimetric assays, among other formats that would be well known to one skilled in the art.

Methods well-known in the art for collecting, handling and processing bodily fluids, such as urine, blood, serum and plasma, and other body fluids, are used in the practice of the present disclosure, for instance, when a truncated DBP (or fusion protein thereof) or a mutated truncated DBP (or fusion protein thereof) according to the present disclosure is employed as an immunodiagnostic reagent, and/or in a vitamin D, specifically 25-hydroxy vitamin D2 and 25-hydroxy vitamin D3, immunoassay kit. The test sample can comprise further moieties in addition to the Vitamin D analytes of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary, such as isolated plasma or serum, pretreatment optionally can be done for mere convenience (e.g., as part of a regimen on a commercial platform). Optionally the test sample is serum.

The pretreatment reagent can be any reagent appropriate for use with the immunoassay and kits of the invention. Since it is known that 25-hydroxy vitamin D analyte, as well as other forms of vitamin D, can bind in vivo to vitamin D binding protein, optionally a pretreatment reagent or method of pretreatment is one that separates analyte binding protein from vitamin D binding protein that is present in vivo. This is described, for example, in U.S. Pat. No. 7,087,395 and U.S. Pat. No. 7,482,162, among other references. Sackrison et al., for example, discloses lowering the pH of the sample to 5.5 or less to dissociate 25-hydroxy vitamin D from vitamin D binding proteins (see, e.g., U.S. Pat. App. Pub. No. 2004/0132104). The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., DBP) present in the sample. Such a pretreatment step comprises removing any analyte binding protein by separating from the precipitated analyte binding protein the supernatant of the mixture formed by the addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for the 25-hydroxy vitamin D2 and 25-hydroxy vitamin D3 (or fragments thereof), such as a labeled anti-analyte monoclonal antibody (or an antigenically reactive fragment thereof), or a labeled DBP (or fragment thereof), such as provided herein. The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 Methylene glycol in the case where organic reagents are used) is still present (or remains) in the test sample mixture during capture.

In a heterogeneous format, after the test sample is obtained from a subject, a first mixture is prepared. The mixture contains the test sample being assessed for 25-hydroxy vitamin $D_2$ and 25-hydroxy vitamin $D_3$ (or fragments thereof) and a first specific binding partner, wherein the first specific binding partner and 25-hydroxy vitamin $D_2$ and 25-hydroxy vitamin $D_3$ (or fragments thereof) contained in the test sample form a first specific binding partner-25-hydroxy vitamin $D_2$ complex and a first specific binding partner-25-hydroxy vitamin $D_3$ complex. Optionally, the first specific binding partner is an anti-analyte antibody or a fragment thereof, or a DBP such as provided herein. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-25-hydroxy vitamin $D_2$ complex and the first specific binding partner-25-hydroxy vitamin $D_3$ complex are formed, any unbound 25-hydroxy vitamin $D_2$ or 25-hydroxy vitamin $D_3$ is removed from the complex using any technique known in the art. For example, the unbound 25-hydroxy vitamin $D_2$ and 25-hydroxy vitamin $D_3$ can be removed by washing. Desirably, however, the first specific binding partner is present in excess of any 25-hydroxy vitamin $D_2$ and 25-hydroxy vitamin $D_3$ present in the test sample, such that all 25-hydroxy vitamin $D_2$ and 25-hydroxy vitamin $D_3$ that is present in the test sample is bound by the first specific binding partner.

After any unbound 25-hydroxy vitamin $D_2$ and 25-hydroxy vitamin $D_3$ are removed, a second specific binding partner is added to the mixture to form a first specific binding partner-25-hydroxy vitamin $D_2$-second specific binding partner complex and a a first specific binding partner-25-hydroxy vitamin $D_3$-second specific binding partner complex. The second specific binding partner is optionally an anti-analyte antibody that binds to an epitope on the analyte of interest that differs from the epitope on the analyte of interest bound by the first specific binding partner. The second binding partner further optionally binds both 25-hydroxy vitamin $D_2$ and 25-hydroxy vitamin $D_3$ and is a DBP as described herein. Moreover, also preferably, the second specific binding partner is labeled with or contains a detectable label as described above. In this regard, if the first specific binding partner is an antibody, then the second specific binding partner preferably is DBP; if the first specific binding partner is DBP, then the second specific binding partner preferably is an antibody.

Any suitable detectable label as is known in the art can be used. For example, the detectable label can be a radioactive label (such as 3H, $^{125}$I, $^{35}$S, $^{14}$C, $^{32}$P, and $^{33}$P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-Vitamin D analyte complexes form. Alternatively, if a second specific binding partner is used and the second specific binding partner is detectably labeled with an acridinium compound, detectably labeled first specific binding partner-Vitamin D analyte-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of 25-hydroxy vitamin $D_2$ and 25-hydroxy vitamin $D_3$ is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of analyte in the sample can be quantified. Specifically, the amount of 25-hydroxy vitamin $D_2$ and 25-hydroxy vitamin $D_3$ in the sample is proportional to the intensity of the signal generated. The amount of 25-hydroxy vitamin $D_2$ and 25-hydroxy vitamin $D_3$ present can be quantified by comparing the amount of light generated to a standard curve for 25-hydroxy vitamin $D_2$ and 25-hydroxy vitamin $D_3$ or by comparison to a reference standard. The standard curve can be generated using serial dilutions or solutions of known concentrations of analyte by mass spectroscopy, gravimetric methods, and other techniques known in the art.

Vitamin D immunoassays generally can be conducted using any format known in the art, such as, but not limited to, a sandwich format, as further described in U.S. Patent Application Publication No. US 2009-0269777, which was published on Oct. 29, 2009, and which is hereby incorporated by reference. Specifically, in one format an antibody that specifically binds to 25-hydroxy vitamin $D_2$ and 25-hydroxy vitamin $D_3$ and a DBP are employed to determine the total amount of 25-hydroxy vitamin $D_2$ and 25-hydroxy vitamin $D_3$ in a sample. More specifically, the antibody and the DBP bind to 25-hydroxy vitamin $D_2$ and 25-hydroxy vitamin $D_3$. Generally, the antibody or DBP used to capture the 25-hydroxy vitamin $D_2$ and 25-hydroxy vitamin $D_3$ in the test sample is referred to as a "capture agent," e.g., a "capture antibody" in the case of an antibody. The antibody or DBP used to bind a detectable and quantifiable label to the sandwich is referred to as the "detection agent," e.g., the "detection antibody" in the case of an antibody, or the "conjugate".

Generally speaking, a sample being tested for (for example, suspected of containing) the 25-hydroxy vitamin $D_2$ and 25-hydroxy vitamin $D_3$ (or fragments thereof) can be contacted with at least one capture agent (e.g., antibody or DBP) and at least one detection agent (e.g., DBP or antibody, respectively), either simultaneously or sequentially and in either order. For example, the test sample can be first contacted with at least one capture agent and then (sequentially) with at least one detection agent. Alternatively, the test sample can be first contacted with at least one detection agent and then (sequentially) with at least one capture agent. In yet another alternative, the test sample can be contacted simultaneously with a capture agent and a detection agent.

In the sandwich assay format, a sample suspected of containing 25-hydroxy vitamin $D_2$ and 25-hydroxy vitamin $D_3$ (or fragments thereof) is first brought into contact with an at least one first capture agent under conditions that allow the formation of a first capture agent/25-hydroxy vitamin $D_2$ complex and first capture agent/25-hydroxy vitamin $D_3$ complex. If more than one capture agent is used, a multiple capture agent/25-hydroxy vitamin $D_2$ complex and multiple capture agent/25-hydroxy vitamin $D_3$ complex are formed. In a sandwich assay, the capture agents are used in molar excess amounts of the maximum amount of 25-hydroxy vitamin $D_2$ and 25-hydroxy vitamin $D_3$ (or fragments thereof) expected in the test sample. For example, from about 5 µg to about 1 mg of capture agent per mL of buffer (e.g., microparticle coating buffer) can be used.

Competitive inhibition immunoassays, which are often used to measure small analytes because binding by only one antibody is required, comprise sequential and classic formats. In a sequential competitive inhibition immunoassay a capture monoclonal antibody to an analyte of interest is coated onto a well of a microtiter plate. When the sample containing the analyte of interest is added to the well, the analyte of interest binds to the capture monoclonal antibody. After washing, a known amount of labeled (e.g., biotin or horseradish peroxidase (HRP)) analyte is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay a monoclonal antibody to an analyte of interest is coated onto a well of a microtiter plate. However, unlike the sequential competitive inhibition immunoassay, the sample and the labeled analyte are added to the well at the same. Any analyte in the sample competes with labeled analyte for binding to the capture monoclonal antibody. After washing, the signal generated by the labeled analyte is measured and is inversely proportional to the amount of analyte in the sample. In an alternative embodiment, a sample can be contacted with a labeled antibody, such as a labeled monoclonal antibody or a labeled polyclonal antibody, which binds to the 25-hydroxy vitamin $D_2$ and 25-hydroxy vitamin $D_3$ (or fragments thereof). Then exogenous 25-hydroxy vitamin $D_2$ and 25-hydroxy vitamin $D_3$, such as a conjugate of 25-hydroxy vitamin $D_2$ and 25-hydroxy vitamin $D_3$, e.g., exogenous 25-hydroxy vitamin $D_2$ conjugated to biotin and exogenous 25-hydroxy vitamin $D_3$ conjugated to biotin, can be added. Afterwards, the resultant mixture, which comprises the sample, the labeled antibody, and the conjugate of exogenous analyte (e.g., exogenous 25-hydroxy vitamin $D_2$ conjugated to biotin and exogenous 25-hydroxy vitamin $D_3$ conjugated to biotin), is contacted with a solid support (e.g., a magnetic bead) to which is attached a binding partner for the conjugated exogenous analyte (e.g., a magnetic bead to which is attached streptavidin). Any labeled antibody, which is not bound by the 25-hydroxy vitamin $D_2$ and 25-hydroxy vitamin $D_3$ in the sample, binds to the conjugated exogenous analyte, which, in turn, binds to the solid support by way of the binding partner for the conjugated exogenous analyte. The amount of label bound to the solid support is then measured. The amount of label is inversely proportional to the amount of analyte of interest in the test sample. See, e.g., European Pat. App. No. 1931711.

Optionally, prior to contacting the test sample with the at least one capture agent, the at least one capture agent can be bound to a solid support, which facilitates the separation of the capture agent/25-hydroxy vitamin $D_2$ and capture agent/25-hydroxy vitamin $D_3$ complex from the test sample. The substrate to which the capture agent is bound can be any suitable solid support or solid phase that facilitates separation of the capture agent-25-hydroxy vitamin $D_2$ complex and capture agent 25-hydroxy vitamin $D_3$ complex from the sample.

Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles or magnetizable microparticles (e.g., microparticles having ferric oxide or chromium oxide cores and homo- or hetero-polymeric coats and radii of about 1-10 microns)). The substrate can comprise a suitable porous material with a suitable surface affinity to bind a capture agent and sufficient porosity to allow access by a detection agent. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the capture agent to the substrate results; alternatively, a chemical coupling agent or other means can be used to bind covalently the capture agent to the substrate, provided that such binding does not interfere with the ability of the capture agent to bind to 25-hydroxy vitamin $D_2$ and 25-hydroxy vitamin $D_3$.

Alternatively, the capture agent can be bound with microparticles, which have been previously coated with streptavidin or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the capture agent. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture agents, such as antibodies (or fragments thereof), each of which is specific for 25-hydroxy vitamin $D_2$ and 25-hydroxy vitamin $D_3$ can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture agent is attached to a mass spectrometry probe as the solid support, the amount of 25-hydroxy vitamin $D_2$ and 25-hydroxy vitamin $D_3$ bound to the probe can be detected by laser desorption-ionization mass spectrometry. Alternatively, a single column can be packed with different beads, which are derivatized with the one or more capture agents, thereby capturing the 25-hydroxy vitamin $D_2$ and 25-hydroxy vitamin $D_3$ in a single place (see, antibody derivatized, bead-based technologies, e.g., the xMAP technology of Luminex (Austin, Tex.)).

After the test sample being assayed for 25-hydroxy vitamin $D_2$ and 25-hydroxy vitamin $D_3$ is brought into contact with at least one capture agent (for example, the first capture antibody), the mixture is incubated in order to allow for the formation of a first capture (or multiple capture agent) complex with 25-hydroxy vitamin $D_2$ and 25-hydroxy vitamin $D_3$. If the test sample is brought into contact with more than one capture agent, then multiple capture agent/25-hydroxy vitamin $D_2$ complexes and multiple capture agent/25-hydroxy vitamin $D_3$ complexes are formed. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture agent/25-hydroxy vitamin $D_2$ complex(es) and capture agent/25-hydroxy vitamin $D_3$ complex(es), the complexes are then contacted with at least one detection agent (under conditions which allow for the formation of a capture agent/25-hydroxy vitamin $D_2$/detection agent complex and a capture agent/25-hydroxy vitamin $D_3$/detection agent complex). If the capture agent/25-hydroxy vitamin $D_2$ complex and the capture agent/25-hydroxy vitamin $D_3$ complex are contacted with more than one detection agent, then multiple capture agent/25-hydroxy vitamin $D_2$/detection agent complexes and multiple capture agent/25-hydroxy vitamin $D_2$/detection agent complexes are formed. As with the capture agent, when the at least one detection agent is brought into contact with the capture agent/25-hydroxy vitamin $D_2$ complex and the capture agent/25-hydroxy vitamin $D_2$ complex, a period of incubation under conditions similar to those described above is required for the formation of the capture agent/25-hydroxy vitamin $D_2$/detection agent complex(es) and the capture agent/25-hydroxy vitamin $D_2$/detection agent complex(es). Preferably, at least one detection agent contains a detectable label. The detectable label can be bound to the at least one detection agent prior to, simultaneously with, or after the formation of the capture agent/25-hydroxy vitamin $D_2$/detection agent complex(es) and the capture agent/25-hydroxy vitamin $D_2$/detection agent complex(es). Any detectable label known in the art can be used (see discussion above, including Polak and Van Noorden (1997) and Haugland (1996)).

The detectable label can be bound to the detection agent either directly or through a coupling agent. An example of a coupling agent that can be used is EDAC (1-ethyl-3-(3-dimethylaminopropyl)carbodiimide, hydrochloride), which is commercially available from Sigma-Aldrich, St. Louis, Mo. Other coupling agents that can be used are known in the art. Methods for binding a detectable label to a detection agent are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The capture agent/25-hydroxy vitamin $D_2$/detection agent complex(es) and the capture agent/25-hydroxy vitamin $D_3$/detection agent complex(es) can be, but do not have to be, separated from the remainder of the test sample prior to quantification of the label. For example, if the at least one capture agent is bound to a solid support, such as a well or a bead, separation can be accomplished by removing the fluid (of the test sample) from contact with the solid support. Alternatively, if the at least one capture agent is bound to a solid support, it can be simultaneously contacted with the test sample and the at least one detection agent to form a capture agent/25-hydroxy vitamin $D_2$/detection agent complex(es) and a capture agent/25-hydroxy vitamin $D_3$/detection agent complex(es), followed by removal of the test sample from contact with the solid support. If the at least one capture agent is not bound to a solid support, then the capture agent/25-hydroxy vitamin $D_2$/detection agent complex(es) and the capture agent/25-hydroxy vitamin $D_3$/detection agent complex(es) do not have to be removed from the test sample for quantification of the amount of the label.

After formation of the labeled capture agent/25-hydroxy vitamin $D_2$/detection agent complex(es) and the labeled capture agent/25-hydroxy vitamin $D_3$/detection agent complex(es), the amount of label in the complex(es) is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of 25-hydroxy vitamin $D_2$ and 25-hydroxy vitamin $D_3$ in the test sample is determined by use of a standard curve that has been generated using serial dilutions of a known concentration of 25-hydroxy vitamin $D_2$ or 25-hydroxy vitamin $D_3$. Other than using serial dilutions of a known concentration of 25-hydroxy vitamin $D_2$ or 25-hydroxy vitamin $D_3$, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

In a forward competitive binding format an aliquot of a known concentration of detectably labeled 25-hydroxy vitamin $D_2$ or 25-hydroxy vitamin $D_3$ is used to compete with 25-hydroxy vitamin $D_2$ and 25-hydroxy vitamin $D_3$ in a test sample for binding to a capture agent, such as an antibody or DBP, which specifically binds to 25-hydroxy vitamin $D_2$ and 25-hydroxy vitamin $D_3$. The capture agent can be simultaneously or sequentially contacted with the test sample and the labeled 25-hydroxy vitamin $D_2$ or 25-hydroxy vitamin $D_3$. The capture agent can be immobilized on a solid support. If desired, the capture agent can be directly immobilized on a solid support or immobilized on a solid support through a linking agent. For example, an antibody or DBP, which specifically binds to 25-hydroxy vitamin $D_2$ and 25-hydroxy vitamin $D_3$, can be immobilized on a solid support by binding to an anti-species antibody (i.e., a linking agent), which is immobilized on the solid support. Two different kinds of complexes may result—a capture agent-labeled 25-hydroxy vitamin $D_2$ (or $D_3$) complex and a capture agent-unlabeled 25-hydroxy vitamin $D_2$ (or $D_3$) complex. The complexes can be, but do not need to be, separated from the remainder of the test sample prior (e.g., separation of the test sample from the solid support) to quantification of the detectable label by comparison to a standard curve, such as a curve generated by a series of calibrators, by mass spectroscopy, gravimetrically or other manner.

In a reverse competition binding format immobilized 25-hydroxy vitamin $D_2$ or 25-hydroxy vitamin $D_3$ can be either sequentially or simultaneously contacted with a test sample and a labeled specific binding partner, such as an antibody or DBP, which specifically binds to 25-hydroxy vitamin $D_2$ and 25-hydroxy vitamin $D_3$. The labeled specific binding partner can bind to the immobilized 25-hydroxy vitamin $D_2$ or 25-hydroxy vitamin $D_3$ or any 25-hydroxy vitamin $D_2$ and 25-hydroxy vitamin $D_3$ that is present in the test sample. The labeled specific binding partner that binds to 25-hydroxy vitamin $D_2$ and 25-hydroxy vitamin $D_3$ that is present in the test sample is separated from the immobilized 25-hydroxy vitamin $D_2$ or 25-hydroxy vitamin $D_3$ along with the remainder of the test sample. The amount of detectable label attached to the immobilized 25-hydroxy vitamin $D_2$ or 25-hydroxy vitamin $D_3$ is then quantified by comparison to a standard curve, such as a curve generated by a series of calibrators, by mass spectroscopy, gravimetrically or other manner.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-capture agent complex is excited by a linearly polarized light, the emitted light remains highly polarized because the fluorophore is constrained from rotating between the time light is absorbed and the time light is emitted. When a "free" tracer compound (i.e., a compound that is not bound to a capture agent) is excited by linearly polarized light, its rotation is much faster than the corresponding tracer-capture agent conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

A commercially available anti-vitamin D antibody, can be used in the methods of assay and kits thereof. Commercially available anti-vitamin D antibodies include those available from Fujirebio and Bioventix. Alternatively, an anti-vitamin D antibody, which is produced in accordance with a method described in the literature, can be used.

Any suitable control composition can be used in the vitamin D immunoassays. The control composition generally comprises 25-hydroxy vitamin $D_2$ or 25-hydroxy vitamin $D_3$ and any desirable additives.

Thus, in view of the above, a method of determining the total amount of 25-hydroxy vitamin $D_2$ and 25-hydroxy vitamin $D_3$ in a test sample is provided. The method comprises:

(i) contacting the test sample with a DBP, wherein the DBP is selected from the group consisting of:
   (a) a truncated DBP consisting essentially of domain I and α-helix 1 of domain II,
   (b) a truncated DBP consisting essentially of amino acids 1-211,
   (c) a truncated DBP consisting essentially of SEQ ID NO:12,
   (d) a mutated truncated DBP consisting essentially of domain I and α-helix 1 of domain II in which amino acid 76 is mutated, amino acid 79 is mutated, or amino acid 76 and amino acid 79 are mutated,
   (e) a mutated truncated DBP consisting essentially of amino acids 1-211 in which amino acid 76 is mutated, amino acid 79 is mutated, or amino acid 76 and amino acid 79 are mutated,
   (f) a mutated truncated DBP consisting essentially of SEQ ID NO:12 in which serine 76 is mutated, serine 79 is mutated, or serine 76 and serine 79 are mutated,
   (g) a mutated truncated DBP consisting essentially of SEQ ID NO:2,
   (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
   (i) a mutated truncated DBP consisting essentially of amino acids 1-267 in which amino acid 76 is mutated, amino acid 79 is mutated, or amino acid 76 and amino acid 79 are mutated,
   (j) a mutated truncated DBP consisting essentially of SEQ ID NO:14 in which serine 76 is mutated, serine 79 is mutated, or serine 76 and serine 79 are mutated,
   (k) a mutated truncated DBP consisting essentially of SEQ ID NO:6, or
   (l) a fusion protein comprising (a), (b), (c), (d), (e), (f), (g), (h), (i), (j), or (k),
whereupon 25-hydroxy vitamin $D_2$ and 25-hydroxy vitamin $D_3$ present in the test sample bind to the DBP, and (ii) detecting the amount of 25-hydroxy vitamin $D_2$ and 25-hydroxy vitamin $D_3$ bound to DBP, wherein the amount of 25-hydroxy vitamin $D_2$ and 25-hydroxy vitamin $D_3$ bound to DBP is indicative of the total amount of 25-hydroxy vitamin $D_2$ and 25-hydroxy vitamin $D_3$ in the test sample.

Also in view of the above, a method of determining the total amount of 25-hydroxy vitamin $D_2$ and 25-hydroxy vitamin $D_3$ in a test sample is also provided. The method comprises (i) contacting the test sample with a solid support, whereupon 25-hydroxy vitamin $D_2$ and 25-hydroxy vitamin $D_3$ present in the test sample bind to the solid support, (ii) separating the solid support and any 25-hydroxy vitamin $D_2$ and 25-hydroxy vitamin $D_3$ that did not bind to the solid support in (i), (iii) contacting the solid support with a detectably labeled antibody that specifically binds to 25-hydroxy vitamin $D_2$ and 25-hydroxy vitamin $D_3$, wherein the antibody can be a monoclonal antibody, a polyclonal antibody, or an antigenically reactive fragment of an antibody, and wherein the antibody binds to an epitope that is not bound by the solid support, (iv) separating the solid support and any detectably labeled antibody that did not bind to 25-hydroxy vitamin $D_2$ and 25-hydroxy vitamin $D_3$ in (iii), and (v) detecting a signal generated by the detectably labeled antibody and, simultaneously or subsequently, comparing the signal generated by the detectably labeled antibody to a signal generated by a control or calibrator, wherein the signal is directly related to the amount of 25-hydroxy vitamin $D_2$ and 25-hydroxy vitamin $D_3$. The solid support comprises (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k). Any of (a)-(k) can be attached to the solid support of step (i) by an anti-DBP antibody or (l) can be attached to the solid support of step (i) by an anti-DBP antibody or an antibody that binds to a protein to which any of (a)-(k) is fused to form the fusion protein of (l). In an embodiment, step (ii), step (iv), or steps (ii) and (iv) is/are not optional (i.e., is/are required). Step (ii), step (iv), or steps (ii) and (iv) can comprise washing the solid support.

Another method of determining the total amount of 25-hydroxy vitamin $D_2$ and 25-hydroxy vitamin $D_3$ in a test sample is also provided. The method comprises (i) contacting the test sample with a solid support, (ii) separating the solid support and any 25-hydroxy vitamin $D_2$ and 25-hydroxy vitamin $D_3$ that did not bind to the solid support in (i), (iii) contacting the solid support with (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k), wherein (a)-(l) are detectably labeled, (iv) separating the solid support and any detectably labeled (a)-(l) that did not bind to 25-hydroxy vitamin $D_2$ and 25-hydroxy vitamin $D_3$ in (iii), and (v) detecting a signal generated by the detectably labeled (a)-(l) and, simultaneously or subsequently, comparing the signal generated by the detectably labeled (a)-(l) to a signal generated by a control or calibrator, wherein the signal is directly related to the amount of 25-hydroxy vitamin $D_2$ and 25-hydroxy vitamin $D_3$. The solid support comprises an antibody that specifically binds to 25-hydroxy vitamin $D_2$ and 25-hydroxy vitamin $D_3$. The antibody can be a monoclonal antibody, a polyclonal antibody, or an antigenically reactive fragment of an antibody, and binds to an epitope that is not bound by (a)-(l). In an embodiment, step (ii), step (iv) or steps (ii) and (iv) is/are not optional (i.e., is/are required). Step (ii), step (iv), or steps (ii) and (iv) can comprise washing the solid support.

Yet another method of determining the total amount of 25-hydroxy vitamin $D_2$ and 25-hydroxy vitamin $D_3$ in a test sample is provided. The method comprises:

(i) contacting the test sample with a DBP, wherein the DBP is selected from the group consisting of:
  (a) a truncated DBP consisting essentially of domain I and α-helix 1 of domain II,
  (b) a truncated DBP consisting essentially of amino acids 1-211,
  (c) a truncated DBP consisting essentially of SEQ ID NO:12,
  (d) a mutated truncated DBP consisting essentially of domain I and α-helix 1 of domain II in which amino acid 76 is mutated, amino acid 79 is mutated, or amino acid 76 and amino acid 79 are mutated,
  (e) a mutated truncated DBP consisting essentially of amino acids 1-211 in which amino acid 76 is mutated, amino acid 79 is mutated, or amino acid 76 and amino acid 79 are mutated,
  (f) a mutated truncated DBP consisting essentially of SEQ ID NO:12 in which serine 76 is mutated, serine 79 is mutated, or serine 76 and serine 79 are mutated,
  (g) a mutated truncated DBP consisting essentially of SEQ ID NO:2,
  (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated,
(i) a mutated truncated DBP consisting essentially of amino acids 1-267 in which amino acid 76 is mutated, amino acid 79 is mutated, or amino acid 76 and amino acid 79 are mutated,
(j) a mutated truncated DBP consisting essentially of SEQ ID NO:14 in which serine 76 is mutated, serine 79 is mutated, or serine 76 and serine 79 are mutated,
(k) a mutated truncated DBP consisting essentially of SEQ ID NO:6, or
(l) a fusion protein comprising (a), (b), (c), (d), (e), (f), (g), (h), (i), (j), or (k), and, simultaneously or sequentially, in either order, contacting the test sample with a specific binding partner for DBP, whereupon 25-hydroxy vitamin $D_2$ and 25-hydroxy vitamin $D_3$ present in the test sample and the specific binding partner for DBP compete for binding to the DBP, and
(ii) detecting the amount of specific binding partner bound to DBP, wherein the amount of specific binding partner bound to DBP is indicative of the total amount of 25-hydroxy vitamin $D_2$ and 25-hydroxy vitamin $D_3$ in the test sample, Yet another method of determining the total amount of 25-hydroxy vitamin $D_2$ and 25-hydroxy vitamin $D_3$ in a test sample is provided. The method comprises (i) contacting a solid support with (i') the test sample and simultaneously or sequentially, in either order, (ii') detectably labeled 25-hydroxy vitamin $D_2$, detectably labeled 25-hydroxy vitamin $D_3$, or detectably labeled 25-hydroxy vitamin $D_2$ and detectably labeled 25-hydroxy vitamin $D_3$, whereupon 25-hydroxy vitamin $D_2$ and 25-hydroxy vitamin $D_3$ present in the test sample and the detectably labeled 25-hydroxy vitamin $D_2$ and/or detectably labeled 25-hydroxy vitamin $D_3$ compete with each other for binding to the solid support, (ii) separating the solid support and any detectably labeled 25-hydroxy vitamin $D_2$ and/or detectably labeled 25-hydroxy vitamin $D_3$ that did not bind to the solid support in (i), and (iii) determining the total amount of 25-hydroxy vitamin $D_2$ and 25-hydroxy vitamin $D_3$ in the test sample based on a signal generated by the detectable label attached to the solid support, wherein the signal generated by the detectable label attached to the solid support is inversely proportional to the total amount of 25-hydroxy vitamin $D_2$ and 25-hydroxy vitamin $D_3$ in the test sample. The solid support comprises (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, or (l) a fusion protein comprising (a), (b), (c), (d), (e), (f), (g), (h), (i), (j), or (k). Any of (a)-(k) can be attached to the solid support of step (i) by an anti-DBP antibody or (l) can be attached to the solid support of step (i) by either of an anti-DBP antibody or an antibody that binds to a protein to which any of (a)-(k) is fused to form the fusion protein of (l). In an embodiment, step (ii) is not optional (i.e., is required). Step (ii) can comprise washing the solid support.

Still yet another method of determining the total amount of 25-hydroxy vitamin $D_2$ and 25-hydroxy vitamin $D_3$ in a test sample is provided. The method comprises (i) contacting a solid support with (i') the test sample and simultaneously or sequentially, in either order, (ii') detectably labeled (m), which is not already bound to 25-hydroxy vitamin $D_2$, 25-hydroxy vitamin $D_3$, or 25-hydroxy vitamin $D_2$ and 25-hydroxy vitamin $D_3$, when the solid support comprises (a), (b), (c), (d), (e), (f), (g), (h), (i), (j), (k), or (l), which is bound to 25-hydroxy vitamin $D_2$, 25-hydroxy vitamin $D_3$, or 25-hydroxy vitamin $D_2$ and 25-hydroxy vitamin $D_3$, or detectably labeled (a), (b), (c), (d), (e), (f), (g), (h), (i), (j), (k), or (l), which is not bound to 25-hydroxy vitamin $D_2$, 25-hydroxy vitamin $D_3$, or 25-hydroxy vitamin $D_2$ and 25-hydroxy vitamin $D_3$, when the solid support comprises (m), which is bound to 25-hydroxy vitamin $D_2$, 25-hydroxy vitamin $D_3$, or 25-hydroxy vitamin $D_2$ and 25-hydroxy vitamin $D_3$, whereupon 25-hydroxy vitamin $D_2$ and 25-hydroxy vitamin $D_3$ present in the test sample and 25-hydroxy vitamin $D_2$ and/or 25-hydroxy vitamin $D_3$ attached to the solid support compete with each other for binding to the detectably labeled (a)-(m) of (ii'), (ii) separating the solid support and any detectably labeled (a)-(m) of (ii') that did not bind to the solid support in (i), and (iii) determining the total amount of 25-hydroxy vitamin $D_2$ and 25-hydroxy vitamin $D_3$ in the test sample based on a signal generated by the detectable label attached to the solid support, wherein the signal generated by the detectable label attached to the solid support is inversely proportional to the total amount of 25-hydroxy vitamin $D_2$ and 25-hydroxy vitamin $D_3$ in the test sample. The solid support comprises (a) a truncated DBP consisting essentially of domain I and α-helix 1 of domain II, (b) a truncated DBP consisting essentially of amino acids 1-211, (c) a truncated DBP consisting essentially of SEQ ID NO:12, (d) a mutated truncated DBP consisting essentially of domain I and α-helix 1 of domain II in which amino acid 76 is mutated, amino acid 79 is mutated, or amino acid 76 and amino acid 79 are mutated, (e) a mutated truncated DBP consisting essentially of amino acids 1-211 in which amino acid 76 is mutated, amino acid 79 is mutated, or amino acid 76 and amino acid 79 are mutated, (f) a mutated truncated DBP consisting essentially of SEQ ID NO:12 in which serine 76 is mutated, serine 79 is mutated, or serine 76 and serine 79 are mutated, (g) a mutated truncated DBP consisting essentially of SEQ ID NO:2, (h) a mutated truncated DBP consisting essentially of domain I and α-helix 1, α-helix 2, α-helix 3, and part or all of α-helix 4 in which amino acid 76 is mutated, amino acid 79 is mutated, or amino acid 76 and amino acid 79 are mutated, (i) a mutated truncated DBP consisting essentially of amino acids 1-267 in which amino acid 76 is mutated, amino acid 79 is mutated, or amino acid 76 and amino acid 79 are mutated, (j) a mutated truncated DBP consisting essentially of SEQ ID NO:14 in which serine 76 is mutated, serine 79 is mutated, or serine 76 and serine 79 are mutated, (k) a mutated truncated DBP consisting essentially of SEQ ID NO:6, (l) a fusion protein comprising (a), (b), (c), (d), (e), (f), (g), (h), (i), (j), or (k), or (m) an antibody that specifically binds to 25-hydroxy vitamin $D_2$ and 25-hydroxy vitamin $D_3$, wherein the antibody can be a monoclonal antibody, a polyclonal antibody, or an antigenically reactive fragment of an antibody, wherein (a)-(m) is bound to 25-hydroxy vitamin $D_2$, 25-hydroxy vitamin $D_3$, or 25-hydroxy vitamin $D_2$ and 25-hydroxy vitamin $D_3$. Any of (a)-(k) can be attached to the solid support of step (i) by an anti-DBP antibody or (l) can be attached to the solid support of step (i) by either of an anti-DBP antibody or an antibody that binds to a protein to which any of (a)-(k) is fused to form the fusion protein of (l). In an embodiment, step (ii) is not optional (i.e., is required). Step (ii) can comprise washing the solid support.

The method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for 25-hydroxy vitamin $D_2$ and 25-hydroxy vitamin $D_3$. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., rickets in children, osteomalcia in adults, hypercalcemia, hypocalcemia, hypercalciuria, hypocalciuria, hyperphosphatemia, hypophosphatemia, parathyroid hormone (PTH) secretion disorder, cellular differentiation or growth disorder, bone formation or metabolism disorder, or kidney function, failure or need for dialysis) or with particular indicia can be made. Typically, the predetermined level is obtained with assays of reference subjects (or populations of subjects). Vitamin D ranges from about 10 mg/L to about 100 mg/L, such as from 20 mg/L to about 75 mg/L, in plasma (serum) of healthy individuals. There is currently debate over the recommended target range of vitamin D in serum, but an expert panel recently suggested a target range of at least from about 30 to about 40 ng/mL (Souberbielle J C, Autoimmun Rev, 9:709-715 (2010)). The serum concentration of 25-hydroxy vitamin $D_2$ and 25-hydroxy vitamin $D_3$ within the normal population has been reported as from 25-80 ng/mL (Mayo Clinic, Mayo Medical Laboratories, www.mayomedicallaboratories.com/test-catalog/Clinical+and+Interpretive/83670). The vitamin D measured can include fragments thereof, degradation products thereof, and/or enzymatic cleavage products thereof.

In particular, with respect to a predetermined level as employed for monitoring disease progression and/or treatment, the amount or concentration of 25-hydroxy vitamin $D_2$ and 25-hydroxy vitamin $D_3$ may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for 25-hydroxy vitamin $D_2$ and 25-hydroxy vitamin $D_3$ is defined in accordance with standard practice. Because the levels of 25-hydroxy vitamin $D_2$ and 25-hydroxy vitamin $D_3$ in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable disease, and a "normal" (sometimes termed "control") patient or population is/are one(s) that exhibit(s) no detectable disease. Furthermore, given that Vitamin D is not routinely found at a high level in the majority of the human population, a "normal subject" can be considered an individual with no substantial detectable increased or elevated amount or concentration of 25-hydroxy vitamin $D_2$ and 25-hydroxy vitamin $D_3$, and a "normal" (sometimes termed "control") patient or population is/are one(s) that exhibit(s) no substantial detectable increased or elevated amount or concentration of 25-hydroxy vitamin $D_2$ and 25-hydroxy vitamin $D_3$. An "apparently normal subject" is one in which 25-hydroxy vitamin $D_2$ and 25-hydroxy vitamin $D_3$ has not been or is being assessed. The level of 25-hydroxy vitamin $D_2$ and 25-hydroxy vitamin $D_3$ is said to be "elevated" when the 25-hydroxy vitamin $D_2$ and 25-hydroxy vitamin $D_3$ is normally undetectable (e.g., the normal level is zero, or within a range of from about 25 to about 75 percentiles of normal populations), but is detected in a test sample, as well as when the 25-hydroxy vitamin $D_2$ and 25-hydroxy vitamin $D_3$ is present in the test sample at a higher than normal level. Thus, inter alia, the disclosure provides a method of screening for a subject having, or at risk of having, e.g., rickets, osteomalcia in adults, hypercalcemia, hypocalcemia, hypercalciuria, hypocalciuria, hyperphosphatemia, hypophosphatemia, parathyroid hormone (PTH) secretion disorder, cellular differentiation or growth disorder, bone formation or metabolism disorder, or kidney function, failure or need for dialysis, for example. Individuals receiving therapy to prevent or treat osteoporosis, elderly individuals with minimal exposure to sunlight, patients with signs and symptoms of hypocalcemia or hypercalcemia, children suspected of having rickets, adults suspected of having osteomalacia, and patients, who are receiving vitamin D therapy and are not demonstrating clinical improvement should be tested for vitamin D deficiency.

In some embodiments, the methods of the disclosure are applied to detect 25-hydroxy vitamin $D_2$ and 25-hydroxy vitamin $D_3$ in samples from patients in need of vitamin D supplementation, including but not limited to healthy subjects and subjects at risk for vitamin D insufficiency or deficiency, for instance, subjects with stage 1, 2, 3, 4 or 5 chronic kidney disease (CKD); subjects with renal osteodystrophy (including osteomalacia and osteitis fibrosa cystica); infants, children and adults that do not drink vitamin D fortified milk (e.g., lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenyloin, fosphenyloin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); and subjects with osteoporosis and/or postmenopausal women.

The method of assay can also involve the assay of other markers and the like. For instance, assay of 25-hydroxy vitamin $D_2$ and 25-hydroxy vitamin $D_3$ can be combined with assay of fertility hormones, thyroid hormones, steroid hormones, kidney function, therapeutic drugs, tumor markers, and other biomarkers and tests.

The order in which the assay of 25-hydroxy vitamin $D_2$ and 25-hydroxy vitamin $D_3$ and other assays are carried out is not critical. Such assays can be carried out simultaneously or sequentially in any order. In addition, the assays can be carried out with the same sample, e.g., in the same reaction vessel or different reaction vessels, or with different samples. For example, the assay of 25-hydroxy vitamin $D_2$ and 25-hydroxy vitamin $D_3$ can be done on a first sample obtained from a subject, and the other assay(s) can be done on a second sample obtained from a subject, or vice versa. The first and second samples obtained from the patient can be obtained at the same time or at different periods of time from one another.

The methods described herein also can be used to determine whether or not a subject has or is at risk of developing a disease or disorder, e.g., rickets, osteomalcia, hypercalcemia, hypocalcemia, hypercalciuria, hypocalciuria, hyperphosphatemia, hypophosphatemia, parathyroid hormone (PTH) secretion disorder, cellular differentiation or growth disorder, bone formation or metabolism disorder, or kidney function, failure or need for dialysis, for example. Specifically, such a method can comprise the steps of:

(a) determining the concentration or amount in a test sample from a subject of an analyte, namely vitamin D (25-hydroxy vitamin $D_2$ and 25-hydroxy vitamin $D_3$), (e.g., using the methods described herein, or methods known in the art); and (b) comparing the concentration or amount of the analyte determined in step (a) with a predetermined level, wherein, if the concentration or amount of the analyte determined in step (a) is favorable with respect to a predetermined level, then the subject is determined not to have or be at risk for a given disease or disorder. However, if the concentration or amount of an analyte determined in step (a) is unfavorable with respect to the predetermined level, then the subject is determined to have or be at risk for a given disease or disorder.

Additionally, provided herein is method of monitoring the progression of a disease or a disorder, e.g., rickets, osteomalcia, hypercalcemia, hypocalcemia, hypercalciuria, hypocalciuria, hyperphosphatemia, hypophosphatemia, parathyroid hormone (PTH) secretion disorder, cellular differentiation or growth disorder, bone formation or metabolism disorder, or kidney function, failure or need for dialysis, in a subject. Optimally, the method comprises the steps of:

(a) determining the concentration or amount in a test sample from a subject of an analyte, namely vitamin D (25-hydroxy vitamin $D_2$ and 25-hydroxy vitamin $D_3$);

(b) determining the concentration or amount in a later test sample from the subject of the analyte; and (c) comparing the concentration or amount of analyte as determined in step (b) with the concentration or amount of analyte determined in step (a), wherein, if the concentration or amount determined in step (b) is unchanged or is unfavorable when compared to the concentration or amount of analyte determined in step (a), then the disease in the subject is determined to have continued, progressed or worsened. By comparison, if the concentration or amount of analyte as determined in step (b) is favorable when compared to the concentration or amount of analyte as determined in step (a), then the disease in the subject is determined to have discontinued, regressed or improved.

Optionally, the method further comprises comparing the concentration or amount of analyte as determined in step (b), for example, with a predetermined level. Further, optionally the method comprises treating the subject with one or more pharmaceutical compositions for a period of time if the comparison shows that the concentration or amount of analyte as determined in step (b), for example, is unfavorably altered with respect to the predetermined level.

Still further, the methods can be used to monitor treatment in a subject receiving treatment with one or more pharmaceutical compositions. In some embodiments, the methods of the disclosure are applied to detect 25-hydroxy vitamin $D_2$ and 25-hydroxy vitamin $D_3$ in samples from patients with vitamin D-responsive diseases, i.e., diseases where administration of Vitamin D or metabolite prevents onset or progression of disease, or reduces signs or symptoms of disease. Such vitamin D-responsive diseases include cancer (e.g. breast, lung, skin, melanoma, colon, colorectal, rectal, prostate and bone cancer), autoimmune diseases (e.g., type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis, and chronic dermatitis), other inflammatory diseases (e.g., asthma, chronic obstructive pulmonary disease, polycystic kidney disease (PKD), polycystic ovary syndrome, pancreatitis, nephritis, hepatitis, and infection), hypertension, cardiovascular diseases including testing samples from subjects at risk of or suffering from cardiovascular diseases (e.g., atherosclerosis, arteriosclerosis, coronary artery disease, cerebrovascular disease, peripheral vascular disease, myocardial infarction, myocardial ischemia, cerebral ischemia, stroke, congestive heart failure, or cardiomyopathy), obesity or other weight disorders, lipid disorders (e.g. hyperlipidemia, dyslipidemia including associated diabetic dyslipidemia and mixed dyslipidemia, hypoalphalipoproteinemia, hypertriglyceridemia, hypercholesterolemia, and low HDL (high density lipoprotein)), metabolic disorders (e.g., Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

Specifically, such methods involve providing a first test sample from a subject before the subject has been administered one or more pharmaceutical compositions. Next, the concentration or amount of analyte, namely vitamin D (25-hydroxy vitamin $D_2$ and 25-hydroxy vitamin $D_3$), in a first test sample from a subject is determined (e.g., using the methods described herein or as known in the art). After the concentration or amount of analyte is determined, optionally the concentration or amount of analyte is then compared with a predetermined level. If the concentration or amount of analyte as determined in the first test sample is lower than the predetermined level, then the subject is not treated with one or more pharmaceutical compositions. However, if the concentration or amount of analyte as determined in the first test sample is higher than the predetermined level, then the subject is treated with one or more pharmaceutical compositions for a period of time. There is no general consensus for a cut-off level for treatment; however, 25-35 ng/mL is considered to be the minimal amount of 25-hydroxy vitamin D needed to avoid adverse effects of deficiency. An expert panel recently suggested a target range of at least from about 30 to about 40 ng/mL (Souberbielle J C, Autoimmun Rev, 9:709-715 (2010)). Assays can be used to establish the need for vitamin D replacement therapy and to guide appropriate treatment, thereby avoiding undermedicating the patient. Overmedication can occur with long-term administration of 10,000 U/day or more and can be detected by assay. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of analyte, namely vitamin D (25-hydroxy vitamin $D_2$ and 25-hydroxy vitamin $D_3$), is determined in the second or subsequent test sample is determined (e.g., using the methods described herein or as known in the art). The concentration or amount of analyte as determined in each of the second and subsequent test samples is then compared with the concentration or amount of analyte as determined in the first test sample (e.g., the test sample that was originally optionally compared to the predetermined level). If the concentration or amount of analyte as determined in step (c) is favorable when compared to the concentration or amount of analyte as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of analyte as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's analyte level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as serum or plasma. Optionally the above assays can then be repeated using a second test sample obtained from the subject where the second test sample is obtained from another source. The results obtained from the assays using the first test sample and the second test sample can be compared. The comparison can be used to assess the status of a disease or condition in the subject.

Moreover, the present disclosure also relates to methods of determining whether a subject predisposed to or suffering from a disease will benefit from treatment. In particular, the disclosure relates to vitamin D companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, a disease or disorder is a candidate for therapy. Generally, the subject is one who has experienced some symptom of the disease or who has actually been diagnosed as having, or being at risk for, such a disease, and/or who demonstrates an unfavorable concentration or amount of an analyte as described herein.

The method optionally comprises an assay as described herein, where analyte, namely vitamin D (25-hydroxy vitamin $D_2$ and 25-hydroxy vitamin $D_3$), is assessed before and following treatment of a subject with one or more pharmaceutical compositions (e.g., particularly with a pharmaceutical related to a mechanism of action involving vitamin D), with immunosuppressive therapy, or by immunoabsorption therapy, or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

It goes without saying that, while certain embodiments herein are advantageous when employed to assess a given disease or disorder, the assays and kits also optionally can be employed to assess an analyte, such as vitamin D, in other diseases, disorders and conditions.

The method of assay also can be used to identify a compound that ameliorates a disease or disorder. For example, a cell that produces an analyte, namely vitamin D (25-hydroxy vitamin $D_2$ and 25-hydroxy vitamin $D_3$), can be contacted with a candidate compound. The level of production of an analyte in the cell contacted with the compound can be compared to that in a control cell using the method of assay described herein.

Furthermore, the vitamin D binding proteins (DBPs) as described herein can be employed not only in assays of vitamin D (any format, not just those set out herein), but also, for any other purpose, e.g., to produce macrophage activating factors, used in cancer, viral infection and osteoporosis treatment, and used in treatment of any other disease, disorder or condition in which they would reasonably be expected to impart a therapeutic benefit.

Adaptation of Kit and Method

The kit (or components thereof), as well as the method of determining the amount of vitamin D, specifically 25-hydroxy vitamin $D_2$ and 25-hydroxy vitamin $D_3$, in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing an analyte of interest is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, analyte, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal antibody as a signal amplifier.

EXAMPLES

The following examples serve to illustrate the present disclosure. The examples are not intended to limit the scope of the claimed invention in any way.

Example 1

This example describes the cloning of full-length and truncated human vitamin D binding protein (hDBP).

The DNA sequence of hDBP from allele GC 1S was obtained from PubMed. The gene, along with its endogenous 16 amino acid signal peptide, was synthesized. The hDBP gene including the signal peptide was cloned in pUC57 plasmid (GenScript USA Inc., Piscataway, N.J.).

The hDBP was truncated in different lengths and displayed on yeast surface to identify the minimal vitamin D binding region. A total of five hDBP truncates and the full-length hDBP (Table I) were cloned into pYD yeast display vector (Invitrogen) by polymerase chain reaction (PCR) and Nco I/Xho I restriction digestion. The full-length hDBP and five truncates displayed on yeast surface at high levels.

TABLE I

Truncation of hDBP in different lengths

| hDBP GC1S | Domain | | |
|---|---|---|---|
| | I | II | III |
| hDBP0 (Full-Length) | 191 | 187 | 80 |
| hDBP1 (Domain 1) | 191 | — | — |
| hDBP2 (Domain 1 less helix 10 of domain 1) | 178 | — | — |
| hDBP3 (Domain I plus helix 1 of domain II) | 191 | 20 | — |
| hDBP4 (Domain I + ~half of domain II) | 191 | 76 | — |
| hDBP5 (Domain I & II less helix 10 of domain II) | 191 | 173 | — |

Example 2

This example describes the binding affinity of full-length and truncated hDBP to 25-hydroxy vitamin $D_3$-3-biotin.

Binding affinity to 25-hydroxy vitamin $D_3$-3-biotin of each construct was measured by ligand titration (Table II). The Ag50 is the value (antigen concentration) generated at 50% of maximal binding signal, thus translating into the highest affinity. This testing was performed similar to that detailed in Friguet et al., J. Immunolog. Methods, 77:305-319 (1985).

It was found that hDBP2, which contained domain I without the last α-helix (amino acids 1-178), did not bind to the ligand. The hDBP1 truncate, which contained domain I, bound to the ligand with reduced affinity compared to full-length hDBP. The hDBP3 truncate, which contained domain I plus the first α-helix of domain II (amino acids 1-211), bound to the ligand with similar affinity to the full-length hDBP. Thus, it was concluded that hDBP3 was the minimal vitamin D binding region that retained binding affinity.

TABLE II

Binding affinity of yeast surface displayed hDBP truncates to 25-OH vitamin $D_3$-3-biotin

| hDBP GC1S | $Ag_{50}$, nM |
|---|---|
| hDBP0 (Full-Length) | 65 |
| hDBP1 | 116 |
| hDBP2 | No binding |
| hDBP3 | 83 |
| hDBP4 | 95 |
| hDBP5 | 143 |

Example 3

This example describes the binding affinity of the hDBP3 truncate to vitamin $D_2$, vitamin $D_3$, 25-hydroxy vitamin $D_2$, and 25-hydroxy vitamin $D_3$.

Binding affinity of the hDBP3 truncate to vitamin $D_2$, vitamin $D_3$, 25-hydroxy vitamin $D_2$, and 25-hydroxy vitamin $D_3$ was determined. It was found that the hDBP3 truncate preferentially bound to hydroxylated vitamin $D_{213}$ (TableIII).

TABLE III

Binding affinity of yeast surface displayed hDBP3 to free vitamin Ds, determined by inhibition assay

| Inhibitor | $K_I$, nM |
|---|---|
| Vitamin $D_2$ | 1,388 |
| Vitamin $D_3$ | 2,974 |
| 25-hydroxy Vitamin $D_2$ | 6.4 |
| 25-hydroxy Vitamin $D_3$ | 3.8 |

Example 4

This example describes the fusion of the hDBP3 truncate and the human IgG1 constant fragment (hFc).

The hDBP3 open reading frame (ORF) was amplified by PCR and linked to hFc, which contained a short hinge region with the first six amino acids deleted (to increase secretion), through SOEing (splicing by overlapping extension) PCR. The fusion protein ORF was cloned in pBOS vector (acquired from Abbott Bioresearch Center, Worcester, Mass.) through Nru I/Not I restriction digestion. Secretion of the fusion protein was directed by IgG heavy chain secretion signal peptide. The fusion protein was produced as a dimer by human embryonic kidney (HEK) 293F transient transfection. However, its reactivity to 25-hydroxy vitamin $D_3$-3-biotin was weak. It was postulated that ligand accessibility was partially blocked by hFc, and extending the hDBP truncate could expose its ligand binding pocket.

Example 5

This example describes the fusion of the hDBP4 truncate and hFc.

The hDBP4 truncate is 56 amino acids longer than the hDBP3 truncate and also retains binding affinity. Thus, it was postulated that an hDBP4-hFc fusion protein would have reduced steric hindrance while still possessing binding affinity. The hDBP4 ORF was amplified from the pYD vector and linked to hFc through SOEing PCR. The fusion protein ORF was cloned in pBOS vector through Nru I/Not I restriction digestion. Secretion of the fusion protein was directed by IgG heavy chain secretion signal peptide. The fusion protein was produced as a dimer by HEK 293F transient transfection. Its reactivity to 25-hydroxy vitamin $D_3$-3-biotin was confirmed by ELISA.

Example 6

This example describes the mutation of the hDBP3 truncate to increase affinity for 25-hydroxy vitamin $D_3$-3-biotin.

The yeast surface-displayed hDBP3 was randomly mutagenized to create a mutation library. The library was screened by one round of Magnetic Activated Cell Sorting (MACS) and two rounds of Fluorescence Activated Cell Sorting (FACS) with equilibrium competition staining. A clone named 3-6 was found to have a six-fold increase in affinity to 25-hydroxy vitamin $D_3$-3-biotin. Mutant 3-6 contained two point mutations (S76A, S79A). Plasmid DNA of this clone was isolated.

Example 7

This example describes the fusion of the hDBP3 mutant 3-6 and hFc with 56 amino acids from hDBP4 on its N-terminus The hDBP3 mutant 3-6 was amplified from a pYD vector. The hFc with 56 amino acids from hDBP4 on its N-terminus was amplified from pBOS hDBP4-hFc. The two fragments were linked together through SOEing PCR. The resulting DNA vector was named pBOS hDBP4-hFc 3-6, which contained the two point mutations (S76A, S79A). The fusion protein was produced as a dimer (M.W. 110,617 Dalton) by HEK 293F transient transfection and stable Chinese hamster ovary (CHO) cell line generation. Reactivity to 25-hydroxy vitamin $D_3$-3-biotin was confirmed and found to be higher than wild-type fusion protein by ELISA.

Example 8

This example describes the development of a stable CHO cell line producing hDBP4-hFc 3-6.

The hDBP4-hFc 3-6 ORF was cloned from pBOS vector into pJV vector (pJV and pBOS vectors were acquired from Abbott Bioresearch Center, Worcester, Mass.) through Srf I/Not I restriction digestion. The resultant vector was named pJV hDBP4-hFc 3-6. The pJV vector contains a murine dihydrofolate reductase (DHFR) gene as a selection marker. CHO cell line B3.2 acquired from the Abbott Bioresearch Center (Worcester, Mass.) and containing a deficient DHFR gene was used for transfection and stable expression. CHO B3.2 was transfected with pJV hDBP4-hFc 3-6 and selected for DHFR+transfectants. The selected transfection pool was subcloned by plating cells in 96-well plates at a amount of a single cell per well. Five subclones were selected (186, 230, 536, 1791, and 1930) for gene amplification with methotrexate based on secretion level ranking. The five subclones were amplified with 20, 100, and 500 nM methotrexate. After gene amplification with 500 nM methotrexate, the 5 subclones were pooled and subcloned again. Subclones 988, 801, 211, 156, and 161 were selected for scale up and serum-free culture medium weaning. It was found that subclone 988 secreted ~193 mg/L hDBP4-hFc 3-6 as measured by HPLC quantitation.

Example 9

This example demonstrates that the hDBP4-hFc 3-6 protein expressed from HEK293 cells is stable.

The hDBP4-hFc 3-6 protein expressed from HEK293 cells was tested for stability. hDBP4-hFc 3-6 protein (about 100 µl of 0.5 mg/ml) was stored at room temperature, 2-8° C., and 37° C. A sample of about 20 µl of hDBP4-hFc 3-6 was taken at day 0, 3, 5, and 7, mixed with 20 µl reduced 2× Laemmli sample buffer, and stored at 2-8° C. until SDS-PAGE gel analysis. SDS-PAGE (4-20%) analysis was performed, and the results showed that there was no degradation, even at 37° C. for 7 days.

Example 10

This example describes the use of the hDBP4-hFc 3-6 protein in an enzyme immunoassay (EIA).

Assay plates were covered with adding 100 µL/well of a 2 µg/mL solution of goat anti-human antibody (AffiniPure goat anti-human IgG, Fc fragment specific, Jackson ImmunoResearch) diluted in PBS. The plates were covered and maintained at 2-8° C. overnight. The hDBP4-hFc 3-6 recombinant proteins expressed by HEK293 or CHO cells were tested, and anti-human IgG m2ak antibody was used as a negative control. The assay plate was blocked by removing goat anti-human Fc antibody; diluted test samples and controls (100 µL/well) were separately added to wells. The plate was incubated for about 15 minutes and then washed. Biotin-labeled 25-hydroxy vitamin $D_3$ analytes (100 µL/well) were added at 2 µg/mL, incubated 30 minutes at room temperature, and then washed. Diluted streptavidin-HRP conjugate (1:1000 dilution) was then added and incubated 10 minutes at room temperature, the plate was then washed. The plate was developed by using O-Phenylenediamine-2HCl(OPD) and read at an optical density of 492 nm The results are depicted in FIG. 15.

Example 11

This example describes an observation on the effect of pretreatment agent in one assay format.

Figure 16:
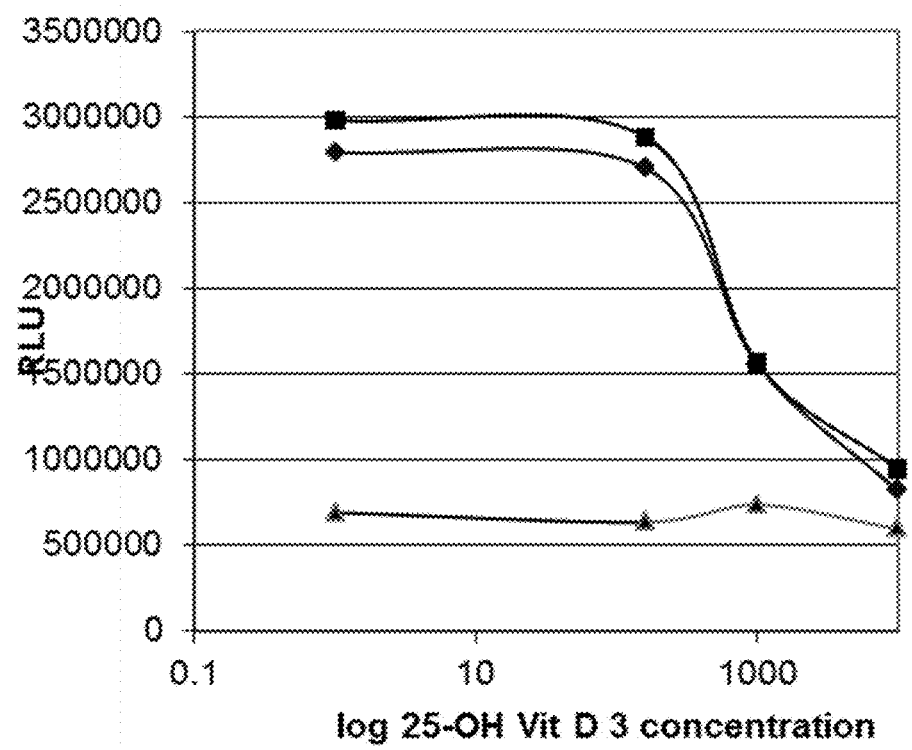
FIG. 16 is a graph showing the effect of sample displacement agent 8-anilino-1-napthalenesulfonic acid ammonium salt (ANSA) on one assay format. Symbols: diamond, hDBP4-hFc 3-6 protein expressed from CHO cells, ANSA-free; square, hDBP4-hFc 3-6 protein expressed from HEK cells, ANSA-free; triangle, hDBP4-hFc 3-6 protein expressed from CHO cells, ANSA-present.

For this study hDBP4-hFc 3-6 protein was coated on microparticles and binding was assessed on the Abbott ARCHITECT instrument to study the effect of adding a non-competitive displacement agent comprising 8-anilino-1-napthalenesulfonic acid ammonium salt (ANSA). ANSA separates any vitamin D metabolite in the sample from vitamin D binding protein to which the vitamin D metabolite is bound, was investigated. Microparticle diluent was used to remove ANSA in one condition (ANSA-free) but not the other (ANSA-present). Results of one such study are depicted in FIG. 16, from which it can be seen that the displacement agent ANSA disturbed the binding of vitamin D from the sample and tracer to the DBP on the solid phase. This suggests that ANSA may optimally need to be removed, an alternative means of pretreatment may be preferred, or that assay reagents may optionally be adjusted, in certain formats using a DBP assay for assessing vitamin D.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A truncated vitamin D binding protein (DBP) comprising an amino acid sequence that is at least 99% identical to the amino acid sequence set forth in SEQ ID NO: 12 or SEQ ID NO: 14 and in which amino acid 76, amino acid 79, or amino acids 76 and 79 are mutated to a different amino acid as compared to SEQ ID NO: 12 or SEQ ID NO: 14, wherein the truncated DBP has vitamin D binding activity.

2. The truncated DBP of claim 1, wherein said truncated DBP is 211 amino acids in length.

3. The truncated DBP of claim 1, wherein said truncated DBP comprises the amino acid sequence set forth in SEQ ID NO: 2.

4. The truncated DBP of claim 1, wherein said truncated DBP is 267 amino acids in length.

5. The truncated DBP of claim 1, wherein said truncated DBP comprises the amino acid sequence set forth in SEQ ID NO: 6.

6. The truncated DBP of claim 1, wherein said truncated DBP is fused to a different protein to form a fusion protein.

7. The truncated DBP of claim 6, wherein said truncated DBP is fused to a different protein to form a fusion protein, wherein said truncated DBP is selected from the group consisting of:
   (a) the truncated DBP is 211 amino acids in length,
   (b) the truncated DBP comprises the amino acid sequence set forth in SEQ ID NO: 2,
   (c) the truncated DBP is 267 amino acids in length, and
   (d) the truncated DBP comprises the amino acid sequence set forth in SEQ ID NO: 6.

8. The truncated DBP of claim 7, wherein said different protein comprises a human IgG1 constant fragment (hFc).

9. The truncated DBP of claim 8, wherein said truncated DBP comprises the amino acid sequence set forth in SEQ ID NO: 10.

10. The truncated DBP of claim 1, wherein said truncated DBP is attached to a solid support.

11. The truncated DBP of claim 10, wherein the truncated DBP is attached to a solid support, wherein the truncated DBP is selected from the group consisting of:
    (a) the truncated DBP is 211 amino acids in length,
    (b) the truncated DBP comprises the amino acid sequence set forth in SEQ ID NO: 2,
    (c) the truncated DBP is 267 amino acids in length,
    (d) the truncated DBP comprises the amino acid sequence set forth in SEQ ID NO: 6, and
    (e) the truncated DBP of (a), (b), (c), or (d) fused to a different protein to form a fusion protein.

12. The truncated DBP of claim 11, wherein said fusion protein comprises a human IgG1 constant fragment (hFc).

13. The truncated DBP of claim 12, wherein said fusion protein comprises the amino acid sequence set forth in SEQ ID NO: 10.

14. The truncated DBP of claim 11, wherein said truncated DBP of (a), (b), (c), or (d) is attached to the solid support by an anti-DBP antibody or said fusion protein of (e) is attached to the solid support by either an anti-DBP antibody or an antibody that binds to a protein to which any of (a), (b), (c), or (d) is fused to form said fusion protein of (e).

15. A kit for assay of 25-hydroxy-vitamin $D_2$ and 25-hydroxy vitamin $D_3$, wherein said kit comprises:
    (i) instructions for assaying a test sample for 25-hydroxy vitamin $D_2$ and 25-hydroxy vitamin $D_3$, and
    (ii) the truncated DBP of claim 1.

16. The kit of claim 15, comprising:
    (i) said instructions for assaying a test sample for 25-hydroxy vitamin $D_2$ and 25-hydroxy vitamin $D_3$ and
    ii) said truncated DBP is selected from one or more of:
       (a) the truncated DBP is 211 amino acids in length,
       (b) the truncated DBP comprises the amino acid sequence set forth in SEQ ID NO:2,
       (c) the truncated DBP is 267 amino acids in length,
       (d) the truncated DBP comprises the amino acid sequence set forth in SEQ ID NO:6,
       (e) a fusion protein comprising the truncated DBP of (a), (b), (c), or (d), and
       (f) a solid support comprising the truncated DBP of (a), (b), (c), or (d), wherein any of (a), (b), (c), or (d) can be detectably labeled.

17. The kit of claim 16, wherein said truncated DBP of (a), (b), (c), or (d) is attached to the solid support by an anti-DBP antibody or said fusion protein of (e) is attached to the solid support by either an anti-DBP antibody or an antibody that binds to a protein to which any of (a), (b), (c), or (d) is fused to form the fusion protein of (e).

18. A method of determining the total amount of 25-hydroxy vitamin $D_2$ and 25-hydroxy vitamin $D_3$ in a test sample, which method comprises:
   (i) contacting the test sample with the truncated DBP of claim 1; and
   (ii) detecting the amount of 25-hydroxy vitamin $D_2$ and 25-hydroxy vitamin $D_3$ bound to said truncated DBP, wherein the amount of 25-hydroxy vitamin $D_2$ and 25-hydroxy vitamin $D_3$ bound to said truncated DBP is indicative of the total amount of 25-hydroxy vitamin $D_2$ and 25-hydroxy vitamin $D_3$ in the test sample, whereupon the total amount of 25-hydroxy vitamin $D_2$ and 25-hydroxy vitamin $D_3$ in the test sample is determined.

19. The method of claim 18, wherein said truncated DBP is selected from the group consisting of:
   (a) the truncated DBP is 211 amino acids in length,
   (b) the truncated DBP comprises the amino acid sequence set forth in SEQ ID NO:2,
   (c) the truncated DBP is 267 amino acids in length,
   (d) the truncated DBP comprises the amino acid sequence set forth in SEQ ID NO:6, and
   (e) a fusion protein comprising the truncated DBP of (a), (b), (c), or (d),
whereupon said 25-hydroxy vitamin $D_2$ and 25-hydroxy vitamin $D_3$ present in said test sample binds to said truncated DBP.

20. The method of claim 18, which wherein said method further comprises:
   (i) contacting the test sample with a solid support, which said solid support comprises said truncated DBP selected from the group consisting of:
      (a) the truncated DBP is 211 amino acids in length,
      (b) the truncated DBP comprises the amino acid sequence set forth in SEQ ID NO:2,
      (c) the truncated DBP is 267 amino acids in length,
      (d) the truncated DBP comprises the amino acid sequence set forth in SEQ ID NO:6, and
      (e) a fusion protein comprising the truncated DBP of (a), (b), (c), or (d),
   whereupon 25-hydroxy vitamin $D_2$ and 25-hydroxy vitamin $D_3$ present in the sample binds to said solid support,
   (ii) optionally separating said solid support and any 25-hydroxy vitamin $D_2$ and 25-hydroxy vitamin $D_3$ that did not bind to the solid support in step (i),
   (iii) contacting said solid support with a detectably labeled antibody that specifically binds to 25-hydroxy vitamin $D_2$ and 25-hydroxy vitamin $D_3$, wherein the antibody can be a monoclonal antibody or a polyclonal antibody,
   (iv) optionally separating said solid support and any detectably labeled antibody that did not bind to 25-hydroxy vitamin $D_2$ and 25-hydroxy vitamin $D_3$ in step (iii), and
   (v) detecting a signal generated by said detectably labeled antibody, and simultaneously or subsequently, comparing the signal generated by the detectably labeled antibody to a signal generated by a control or calibrator, wherein said signal is directly related to the amount of 25-hydroxy vitamin $D_2$ and 25-hydroxy vitamin $D_3$,
   whereupon the total amount of 25-hydroxy vitamin $D_2$ and 25-hydroxy vitamin $D_3$ in the test sample is determined.

21. The method of claim 20, wherein said truncated DBP of (a), (b), (c), or (d) is attached to the solid support of step (i) by an anti-DBP antibody or said fusion protein of (e) is attached to the solid support of step (i) by either an anti-DBP antibody or an antibody that binds to a protein to which the truncated DBP of any of (a), (b), (c), or (d) is fused to form the fusion protein of (e).

22. The method of claim 20, wherein step (ii), step (iv), or steps (ii) and (iv) are required.

23. The method of claim 22, wherein step (ii), step (iv) or steps (ii) and (iv) comprise(s) washing said solid support.

* * * * *

SEQUENCE LISTING

```
<160> NUMBER OF SEQ ID NOS: 17

<210> SEQ ID NO 1
<211> LENGTH: 633
<212> TYPE: DNA
<213> ORGANISM: Homo sapiens

<400> SEQUENCE: 1
ttagagagag gccgggatta tgaaaagaat aaagtctgca aggaattctc ccatctggga      60
aaggaggact tcacatctct gtcactagtc ctgtacagta gaaaatttcc cagtggcacg     120
tttgaacagg tcagccaact tgtgaaggaa gttgtctcct tgaccgaagc ctgctgtgcg     180
```

```
gaaggggctg accctgactg ctatgacacc aggacctcag cactggctgc caaggcctgt      240
gaaagtaatt ctccattccc cgttcaccca ggcactgctg agtgctgcac caaagagggc      300
ctggaacgaa agctctgcat ggctgctctg aacaccagc cacaggaatt ccccacctac       360
gtggaaccca caaatgatga aatctgtgag gcgttcagga agatccaaa ggaatatgct        420 aatcaattta tgtgggaata ttccactaat tacggccaag ctcctctgtc acttttagtc       480
agttacacca agagttatct ttctatggta gggtcctgct gtacctctgc aagcccaact       540
gtatgctttt tgaaagagag actccagctt aaacatttat cacttctcac cactctgtca       600
aatagagtct gctcacaata tgctgcttat ggg                                   633
```

<210> SEQ ID NO 2
<211> LENGTH: 211
<212> TYPE: PRT
<213> ORGANISM: Homo sapiens

<400> SEQUENCE: 2

```
Leu Glu Arg Gly Arg Asp Tyr Glu Lys Asn Lys Val Cys Lys Glu Phe
1               5                   10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
    50                  55                  60

Pro Asp Cys Tyr Asp Thr Arg Thr Ser Ala Leu Ala Ala Lys Ala Cys
65                  70                  75                  80

Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
    130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly
    210
```

<210> SEQ ID NO 3
<211> LENGTH: 168
<212> TYPE: DNA
<213> ORGANISM: Homo sapiens

<400> SEQUENCE: 3

```
gagaagaaat caaggctcag caatctcata aagttagccc aaaaagtgcc tactgctgat      60
ctggaggatg ttttgccact agctgaagat attactaaca tcctctccaa atgctgtgag     120
tctgcctctg aagattgcat ggccaaagag ctgcctgaac acacagta                  168
```

<210> SEQ ID NO 4
<211> LENGTH: 56
<212> TYPE: PRT
<213> ORGANISM: Homo sapiens

<400> SEQUENCE: 4

```
Glu Lys Lys Ser Arg Leu Ser Asn Leu Ile Lys Leu Ala Gln Lys Val
1               5                   10                  15

Pro Thr Ala Asp Leu Glu Asp Val Leu Pro Leu Ala Glu Asp Ile Thr
            20                  25                  30

Asn Ile Leu Ser Lys Cys Cys Glu Ser Ala Ser Glu Asp Cys Met Ala
        35                  40                  45

Lys Glu Leu Pro Glu His Thr Val
    50                  55
```

<210> SEQ ID NO 5
<211> LENGTH: 801
<212> TYPE: DNA
<213> ORGANISM: Homo sapiens

<400> SEQUENCE: 5

```
ttagagagag gccgggatta tgaaaagaat aaagtctgca aggaattctc ccatctggga      60
aaggaggact tcacatctct gtcactagtc ctgtacagta gaaaatttcc cagtggcacg     120
tttgaacagg tcagccaact tgtgaaggaa gttgtctcct tgaccgaagc ctgctgtgcg     180
gaagggctg accctgactg ctatgacacc aggacctcag cactggctgc caaggcctgt     240
gaaagtaatt ctccattccc cgttcaccca ggcactgctg agtgctgcac aaagagggc     300
ctggaacgaa agctctgcat ggctgctctg aaacaccagc cacaggaatt ccccaccttac    360
gtggaaccca caaatgatga atctgtgag gcgttcagga agatccaaa ggaatatgct       420
aatcaattta tgtgggaata ttccactaat tacggccaag ctcctctgtc acttttagtc     480
agttacacca agagttatct ttctatggta gggtcctgct gtacctctgc aagcccaact    540
gtatgctttt tgaaagagag actccagctt aaacatttat cacttctcac cactctgtca   600
aatagagtct gctcacaata tgctgcttat ggggagaaga atcaaggct cagcaatctc     660
ataaagttag cccaaaaagt gcctactgct gatctggagg atgttttgcc actagctgaa    720
gatattacta acatcctctc caaatgctgt gagtctgcct ctgaagattg catggccaaa    780
gagctgcctg aacacacagt a                                              801
```

<210> SEQ ID NO 6
<211> LENGTH: 267
<212> TYPE: PRT
<213> ORGANISM: Homo sapiens

<400> SEQUENCE: 6

```
Leu Glu Arg Gly Arg Asp Tyr Glu Lys Asn Lys Val Cys Lys Glu Phe
1               5                   10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
    50                  55                  60

Pro Asp Cys Tyr Asp Thr Arg Thr Ser Ala Leu Ala Ala Lys Ala Cys
65                  70                  75                  80
```

```
Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
    130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly Glu Lys Lys Ser Arg Leu Ser Asn Leu Ile Lys Leu Ala
    210                 215                 220

Gln Lys Val Pro Thr Ala Asp Leu Glu Asp Val Leu Pro Leu Ala Glu
225                 230                 235                 240

Asp Ile Thr Asn Ile Leu Ser Lys Cys Cys Glu Ser Ala Ser Glu Asp
                245                 250                 255

Cys Met Ala Lys Glu Leu Pro Glu His Thr Val
            260                 265

<210> SEQ ID NO 7
<211> LENGTH: 681
<212> TYPE: DNA
<213> ORGANISM: Homo sapiens

<400> SEQUENCE: 7
aaaactcaca catgcccacc gtgcccagca cctgaactcc tggggggacc gtcagtcttc      60
ctcttccccc caaaacccaa ggacaccctc atgatctccc ggacccctga ggtcacatgc     120
gtggtggtgg acgtgagcca cgaagaccct gaggtcaagt tcaactggta cgtggacggc     180
gtggaggtgc ataatgccaa gacaaagccg cgggaggagc agtacaacag cacgtaccgt     240
gtggtcagcg tcctcaccgt cctgcaccag gactggctga atggcaagga gtacaagtgc     300
aaggtctcca acaaagccct cccagccccc atcgagaaaa ccatctccaa agccaaaggg     360
cagccccgag aaccacaggt gtacaccctg cccccatccc gcgaggagat gaccaagaac     420
caggtcagcc tgacctgcct ggtcaaaggc ttctatccca gcgacatcgc cgtggagtgg     480
gagagcaatg ggcagccgga gaacaactac aagaccacgc ctcccgtgct ggactccgac     540
ggctccttct tcctctacag caagctcacc gtggacaaga gcaggtggca gcaggggaac     600
gtcttctcat gctccgtgat gcatgaggct ctgcacaacc actacacgca gaagagcctc     660
tccctgtctc cgggtaaatg a                                                681

<210> SEQ ID NO 8
<211> LENGTH: 226
<212> TYPE: PRT
<213> ORGANISM: Homo sapiens
```

<400> SEQUENCE: 8

```
Lys Thr His Thr Cys Pro Pro Cys Pro Ala Pro Glu Leu Leu Gly Gly
1               5                   10                  15
Pro Ser Val Phe Leu Phe Pro Pro Lys Pro Lys Asp Thr Leu Met Ile
            20                  25                  30
Ser Arg Thr Pro Glu Val Thr Cys Val Val Val Asp Val Ser His Glu
        35                  40                  45
Asp Pro Glu Val Lys Phe Asn Trp Tyr Val Asp Gly Val Glu Val His
    50                  55                  60
Asn Ala Lys Thr Lys Pro Arg Glu Glu Gln Tyr Asn Ser Thr Tyr Arg
65                  70                  75                  80
Val Val Ser Val Leu Thr Val Leu His Gln Asp Trp Leu Asn Gly Lys
                85                  90                  95
Glu Tyr Lys Cys Lys Val Ser Asn Lys Ala Leu Pro Ala Pro Ile Glu
            100                 105                 110
Lys Thr Ile Ser Lys Ala Lys Gly Gln Pro Arg Glu Pro Gln Val Tyr
        115                 120                 125
Thr Leu Pro Pro Ser Arg Glu Glu Met Thr Lys Asn Gln Val Ser Leu
    130                 135                 140
Thr Cys Leu Val Lys Gly Phe Tyr Pro Ser Asp Ile Ala Val Glu Trp
145                 150                 155                 160
Glu Ser Asn Gly Gln Pro Glu Asn Asn Tyr Lys Thr Thr Pro Pro Val
                165                 170                 175
Leu Asp Ser Asp Gly Ser Phe Phe Leu Tyr Ser Lys Leu Thr Val Asp
            180                 185                 190
Lys Ser Arg Trp Gln Gln Gly Asn Val Phe Ser Cys Ser Val Met His
        195                 200                 205
Glu Ala Leu His Asn His Tyr Thr Gln Lys Ser Leu Ser Leu Ser Pro
    210                 215                 220
Gly Lys
225
```

<210> SEQ ID NO 9
<211> LENGTH: 1482
<212> TYPE: DNA
<213> ORGANISM: Homo sapiens

<400> SEQUENCE: 9

```
ttagagagag gccgggatta tgaaaagaat aaagtctgca aggaattctc ccatctggga      60
aaggaggact tcacatctct gtcactagtc ctgtacagta gaaatttcc cagtggcacg     120
tttgaacagg tcagccaact tgtgaaggaa gttgtctcct tgaccgaagc ctgctgtgcg    180
gaagggctg accctgactg ctatgacacc aggacctcag cactggctgc caaggcctgt    240
gaaagtaatt ctccattccc cgttcaccca ggcactgctg agtgctgcac caaagagggc   300
ctggaacgaa agctctgcat ggctgctctg aacaccagc acaggaatt ccccacctac     360
gtggaaccca caatgatga atctgtgag gcgttcagga agatccaaa ggaatatgct      420
aatcaattta tgtgggaata ttccactaat tacggccaag ctcctctgtc acttttagtc   480
agttacacca agagttatct ttctatggta gggtcctgct gtacctctgc aagcccaact   540
gtatgctttt tgaaagagag actccagctt aaacatttat cacttctcac cactctgtca   600
aatagagtct gctcacaata tgctgcttat ggggagaaga aatcaaggct cagcaatctc   660
ataaagttag cccaaaaagt gcctactgct gatctggagg atgtttttgcc actagctgaa   720
```

```
gatattacta acatcctctc caaatgctgt gagtctgcct ctgaagattg catggccaaa      780
gagctgcctg aacacacagt aaaaactcac acatgcccac cgtgcccagc acctgaactc      840
ctggggggac cgtcagtctt cctcttcccc ccaaaaccca aggacaccct catgatctcc      900
cggacccctg aggtcacatg cgtggtggtg gacgtgagcc acgaagaccc tgaggtcaag      960
ttcaactggt acgtggacgg cgtggaggtg cataatgcca agacaaagcc gcgggaggag     1020
cagtacaaca gcacgtaccg tgtggtcagc gtcctcaccg tcctgcacca ggactggctg     1080
aatggcaagg agtacaagtg caaggtctcc aacaaagccc tcccagcccc catcgagaaa     1140
accatctcca aagccaaagg gcagccccga gaaccacagg tgtacaccct gcccccatcc     1200
cgcgaggaga tgaccaagaa ccaggtcagc ctgacctgcc tggtcaaagg cttctatccc     1260
agcgacatcg ccgtggagtg ggagagcaat gggcagccgg agaacaacta caagaccacg     1320
cctcccgtgc tggactccga cggctccttc ttcctctaca gcaagctcac cgtggacaag     1380
agcaggtggc agcaggggaa cgtcttctca tgctccgtga tgcatgaggc tctgcacaac     1440
cactacacgc agaagagcct ctccctgtct ccgggtaaat ga                         1482
```

<210> SEQ ID NO 10
<211> LENGTH: 493
<212> TYPE: PRT
<213> ORGANISM: Homo sapiens

<400> SEQUENCE: 10

```
Leu Glu Arg Gly Arg Asp Tyr Glu Lys Asn Lys Val Cys Lys Glu Phe
1               5                   10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
    50                  55                  60

Pro Asp Cys Tyr Asp Thr Arg Thr Ser Ala Leu Ala Ala Lys Ala Cys
65                  70                  75                  80

Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
    130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly Glu Lys Lys Ser Arg Leu Ser Asn Leu Ile Lys Leu Ala
    210                 215                 220

Gln Lys Val Pro Thr Ala Asp Leu Glu Asp Val Leu Pro Leu Ala Glu
225                 230                 235                 240
```

```
Asp Ile Thr Asn Ile Leu Ser Lys Cys Cys Glu Ser Ala Ser Glu Asp
                245                 250                 255

Cys Met Ala Lys Glu Leu Pro Glu His Thr Val Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 11
<211> LENGTH: 633
<212> TYPE: DNA
<213> ORGANISM: Homo sapiens

<400> SEQUENCE: 11
ttagagagag gccgggatta tgaaaagaat aaagtctgca aggaattctc ccatctggga      60
aaggaggact tcacatctct gtcactagtc ctgtacagta gaaatttcc cagtggcacg      120 tttgaacagg tcagccaact tgtgaaggaa gttgtctcct tgaccgaagc ctgctgtgcg     180 gaagggctg  accctgactg ctatgacacc aggacctcag cactgtctgc caagtcctgt     240
gaaagtaatt ctccattccc cgttcaccca ggcactgctg agtgctgcac caaagagggc     300
ctggaacgaa agctctgcat ggctgctctg aaacaccagc cacaggaatt ccccacctac     360
gtggaaccca caatgatga  aatctgtgag gcgttcagga agatccaaa  ggaatatgct     420 aatcaattta tgtgggaata ttccactaat tacggccaag ctcctctgtc acttttagtc     480
agttacacca agagttatct ttctatggta gggtcctgct gtacctctgc aagcccaact     540
gtatgctttt tgaaagagag actccagctt aaacatttat cacttctcac cactctgtca    600
aatagagtct gctcacaata tgctgcttat ggg                                  633
```

<210> SEQ ID NO 12
<211> LENGTH: 211
<212> TYPE: PRT
<213> ORGANISM: Homo sapiens

<400> SEQUENCE: 12

Leu Glu Arg Gly Arg Asp Tyr Glu Lys Asn Lys Val Cys Lys Glu Phe
1               5                   10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
    50                  55                  60

Pro Asp Cys Tyr Asp Thr Arg Thr Ser Ala Leu Ser Ala Lys Ser Cys
65                  70                  75                  80

Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
    130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly
210

<210> SEQ ID NO 13
<211> LENGTH: 801
<212> TYPE: DNA
<213> ORGANISM: Homo sapiens

<400> SEQUENCE: 13
ttagagagag gccgggatta tgaaaagaat aaagtctgca aggaattctc ccatctggga      60
aaggaggact tcacatctct gtcactagtc ctgtacagta gaaatttcc cagtggcacg     120 tttgaacagg tcagccaact tgtgaaggaa gttgtctcct tgaccgaagc tgctgtgcg     180 gaagggctg accctgactg ctatgacacc aggacctcag cactgtctgc caagtcctgt     240
gaaagtaatt ctccattccc cgttcaccca ggcactgctg agtgctgcac aaagagggc     300 ctggaacgaa agctctgcat ggctgctctg aaaccaccagc cacaggaatt ccccacctac     360
gtggaaccca caaatgatga aatctgtgag gcgttcagga agatccaaa ggaatatgct     420 aatcaattta tgtgggaata ttccactaat tacggccaag ctcctctgtc acttttagtc     480
agttacacca agagttatct ttctatggta gggtcctgct gtacctctgc aagcccaact     540
gtatgctttt tgaaagagag actccagctt aaacatttat cacttctcac cactctgtca     600
aatagagtct gctcacaata tgctgcttat ggggagaaga aatcaaggct cagcaatctc     660

```
ataaagttag cccaaaaagt gcctactgct gatctggagg atgttttgcc actagctgaa      720
gatattacta acatcctctc caaatgctgt gagtctgcct ctgaagattg catggccaaa      780
gagctgcctg aacacacagt a                                                801
```

<210> SEQ ID NO 14
<211> LENGTH: 267
<212> TYPE: PRT
<213> ORGANISM: Homo sapiens

<400> SEQUENCE: 14

```
Leu Glu Arg Gly Arg Asp Tyr Glu Lys Asn Lys Val Cys Lys Glu Phe
1               5                   10                  15

Ser His Leu Gly Lys Glu Asp Phe Thr Ser Leu Ser Leu Val Leu Tyr
            20                  25                  30

Ser Arg Lys Phe Pro Ser Gly Thr Phe Glu Gln Val Ser Gln Leu Val
        35                  40                  45

Lys Glu Val Val Ser Leu Thr Glu Ala Cys Cys Ala Glu Gly Ala Asp
    50                  55                  60

Pro Asp Cys Tyr Asp Thr Arg Thr Ser Ala Leu Ser Ala Lys Ser Cys
65                  70                  75                  80

Glu Ser Asn Ser Pro Phe Pro Val His Pro Gly Thr Ala Glu Cys Cys
                85                  90                  95

Thr Lys Glu Gly Leu Glu Arg Lys Leu Cys Met Ala Ala Leu Lys His
            100                 105                 110

Gln Pro Gln Glu Phe Pro Thr Tyr Val Glu Pro Thr Asn Asp Glu Ile
        115                 120                 125

Cys Glu Ala Phe Arg Lys Asp Pro Lys Glu Tyr Ala Asn Gln Phe Met
    130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
            180                 185                 190

Leu Ser Leu Leu Thr Thr Leu Ser Asn Arg Val Cys Ser Gln Tyr Ala
        195                 200                 205

Ala Tyr Gly Glu Lys Lys Ser Arg Leu Ser Asn Leu Ile Lys Leu Ala
    210                 215                 220

Gln Lys Val Pro Thr Ala Asp Leu Glu Asp Val Leu Pro Leu Ala Glu
225                 230                 235                 240

Asp Ile Thr Asn Ile Leu Ser Lys Cys Cys Glu Ser Ala Ser Glu Asp
                245                 250                 255

Cys Met Ala Lys Glu Leu Pro Glu His Thr Val
            260                 265
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

```
His His His His His His
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Asp Asp Asp Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Asp Asp Asp Asp Lys
1               5
```